United States Patent [19]
Cho-Chung

[11] Patent Number: 6,060,310
[45] Date of Patent: May 9, 2000

[54] TRANSCRIPTION FACTOR DECOY AND TUMOR GROWTH INHIBITOR

[76] Inventor: Yoon S. Cho-Chung, Bethesda, Md.

[21] Appl. No.: 08/977,643

[22] Filed: Nov. 24, 1997

[51] Int. Cl.[7] .............................. C12N 5/06; C12N 5/10; A61K 31/70; C07H 21/00
[52] U.S. Cl. ........................... 435/375; 514/44; 536/24.5
[58] Field of Search .................................. 435/6, 29, 325, 435/375; 514/44; 536/23.1, 24.5

[56] References Cited

U.S. PATENT DOCUMENTS

| | | |
|---|---|---|
| 4,683,195 | 7/1987 | Mullis et al. . |
| 4,683,202 | 7/1987 | Mullis . |
| 4,873,191 | 10/1989 | Wagner et al. . |
| 4,965,188 | 10/1990 | Mullis et al. . |
| 5,322,770 | 6/1994 | Gelfand . |
| 5,641,486 | 6/1997 | Hinrichs et al. ...................... 424/139.1 |
| 5,683,985 | 11/1997 | Chu et al. .................................. 514/44 |

FOREIGN PATENT DOCUMENTS

| | | |
|---|---|---|
| 90/08832 | of 1990 | WIPO . |
| 92/18522 | of 1992 | WIPO . |

OTHER PUBLICATIONS

Agadir et al., "Retinyl Methyl Ether Down–Regulates Activator Protein 1 Transcriptional Activation in Breast Cancer Cells," *Cancer Research* 57:3444–3450 [1997].
Agrawal et al., "Oligodeoxynucleoside phosphoramidates and phosphorothioates as inhibitors of human immunodeficiency virus," *Proc. Natl. Acad. Sci.* 85:7079–7083 [1988].
Anderson and Young, Quantitative Filter Hybridization, in *Nucleic Acid Hybridization* [1995].
Bielinska et al., "Regulation of Gene Expression with Double–Stranded Phosphorothioate Oligonucleotides," *Science*, 250:997–1000 [1990].
Boshart et al., "A Very Strong Enhancer Is Located Upstream of an Immediate Early Gene of Human Cytomegalovirus," *Cell* 41:521–530 [1985].
Bradley et al., "Formation of germ–line chimaeras from embryo–derived teratocarcinoma cell lines," *Nature* 309:253–254 [1994].
Brinster et al., "Factors affecting the efficiency of introducing foreign DNA into mice by microinjecting eggs," *Proc. Natl. Acad. Sci. USA* 82;4438–4442 [1985].
Chamberlin et al., "New RNA Polymerase from *Escherichia coli* infected with Bacteriophage T7," *Nature* 228:227–231 [1970].
Comb et al., "Proteins bound at adjacent DNA elements act synergistically to regulate human proenkephalin cAMP inducible transcrption," *EMBO J.* 7:3793–3805 [1988].
Comb et al., "A cyclic AMP– and phorbol ester–inducible DNA element," *Nature* 323:353–356 [1986].
Crooke, "Therapeutic Applications of Oligonucleotides," *Annu. Rev. Pharmacol. Toxicol.* 32:329–376 [1992].
Dignam et al., "Accurate transcription initiation by RNA polymerase II in a soluble extract from isolated mammalian nuclei," *Nucleic Acid Res.* 11:1475–1489 [1983].
Dijkema et al., "Cloning and expression of the chromosomal immune interferon gene of the rate," *EMBO J.* 4:761–767 [1985].
Dressler and Potter, "Molecular Mechanisms in Genetic Recombination," *Annu. Rev. Biochem.* 51:727–761 [1982].
Erlich (ed.), *PCR Technology*, Stockton Press [1989].
Evans et al., "Establishment in culture of pluripotential cells from mouse embryos", *Nature* 292:154–156 [1981].
Fried and Crothers, "Equilibria and kinetics of lac repressor–operator interactions by polyacrylamide gel electrophoresis," *Nucleic Acid Res.* 9:6505–6523 [1981].
Friedman et al., "Expression of a truncated vital trans–activator selectively impedes lytic infection by its cognate virus," *Nature* 335:452–454 [1988].
Gacy and McMurray, "Hairpin Formation within the Human Enkephalin Enhancer Region. 1. Kinetic Analysis," *Biochemistry* 33:11951–11959 [1994].
Gellert et al., "DNA Gyrase and DNA Supercoiling," *Cold Spring Harbor Symp. Quant. Biol.* 43:35–40 [1978].
Gonzalez and Montminy, "Cyclic AMP Stimulates Somatostatin gene Transcription by Phosphorylation of CREB at Serine 133," *Cell* 59:675–680 [1989].
Gorman et al., "The Rous sarcoma virus long terminal repeat is a strong promoter when introduced into a variety of eukaryotic cells by DNA–mediated transfection," *Proc. Natl. Acad. Sci. USA* 79:6777–6781 [1982].
Gorman, "High efficiency gene transfer into mammalian cells," in *DNA Cloning*, vol. II, pp. 143–190, IRL press, Oxford, England [1985].
Gossler et al., "Transgenesis by means of blastocyst–derived embyronic stem cell lines," *Proc. Acad. Sci. USA* 83:9065–9069 [1986].
Graham and van der Eb, "A New Technique for the Assay of Infectivity of Human Adenovirus 5 DNA," *Virol.* 52:456–467 [1973].
Gu et al., "Synergistic Activation of Transcription by CBP and p53," *Nature* 387:819–823 [1997].
Gura, "Antisense Has Growing Pains: Efforts to develop antisense compounds as therapies for cancer, AIDS, and other diseases have encountered some unexpected questions about how the drugs really work," *Science* 270:575–577 [1995].
Haldar et al., "Purification and Characterization of the bcl–2 Protein," *Arch. Biochem. Biophys.* 315:483–488 [1994].
Haldar et al., "Down–Regulation of bcl–2 by p53 in Breast Cancer Cells," *Cancer Res.* 54:2095–2097 [1994].

(List continued on next page.)

*Primary Examiner*—John S. Brusca
*Assistant Examiner*—Thomas G. Larson

[57] ABSTRACT

The present invention provides compositions with high affinity for a target transcription factor, that can be introduced into cells as decoy cis-elements to bind the factor and alter gene expression. Specifically, the present invention provides nucleic acid molecules that compete with cAMP response element (CRE) enhancers for binding to transcription factors.

23 Claims, 7 Drawing Sheets

OTHER PUBLICATIONS

Haskell and Bowen, "Efficient Production of Transgenic Cattle by Retroviral Infection of Early Embyros," *Mol. Reprod. Dev.* 40:386–390 [1995].

Hogan et al., in *Manipulating the Mouse Embryo*, Cold Spring Harbor Laboratory Press, Cold Spring Harbor, N.Y. [1986].

Holliday, "A Mechanism for gene conversion in fungi," *Genet. Res.* 5:282–304 [1964].

Horwitz and Loeb, "An *E. coli* Promoter That Regulates Transcription by DNA Superhelix–Induced Cruciform Extrusion," *Science* 241:703–705 [1988].

Jaenisch, "Transgenic Animals," *Science* 240:1468–1474 [1988].

Jaenisch, "Germ line integration and Mendelian transmission of the exogenous Moloney leukemia virus," *Proc. Natl. Acad. Sci. USA* 73:1260–1264 [1976].

Jahner et al., "De novo methylation and expression of retroviral genomes during mouse embyrogenesis," *Nature* 298:623–628 [1982].

Jahner et al., "Insertion of the bacterial gpt gene into the germ line of mice by retroviral infection," *Proc. Natl. Acad Sci. USA* 82:6927–693 [1985].

Kacian et al., "A Replicating RNA Molecule Suitable for a Detailed Analysis of Extracellular Evolution and Replication," *Proc. Natl. Acad. Sci. USA* 69:3038–3042 [1972].

Keleher et al., "The Yeast Cell–Type Specific Repressor α2 Acts Copperatively with a Non–Cell–Type Specific Protein," *Cell* 53:927–936 [1988].

Kim et al., "Use of the human elongation factor 1α promoter as a versatile and efficient expression system," *Gene* 91:217–223 [1990].

Kwast–Welfeld et al., "Evidence that an Additional Conserved Element with the Consensus $^C/_GAG^A/_C$ is Essential for Maximal Responsiveness of the Cyclic AMP Enhancer," *Cellular and Molecular Biology Research* 39:231–242 [1993].

Lenardo et al., "NF–κB protein purification from bovine spleen: Nucleotide stimulation and binding site specificity," *Proc. Natl. Acad. Sci.* 85:8825–8829 [1988].

Maher III et al., "Inhibition of DNA Binding Proteins by Oligonucleotide–Directed Triple Helix Formation," *Science* 245:725–730 [1989].

Maniatis et al., "Regulation of Inducible and Tissue–Specific Gene Expression," *Science* 236:1237–1245 [1997].

McMurray et al., "Hairpin formation with the Human Enkephalin Enhancer Region. 2. Structural Studies," *Biochem.* 33:11960–11970 [1994].

McMurray et al., "Hairpin formation within the enhancer region of the human enkephalin gene," *Proc. Natl. Acad. Sci. USA* 88:666–670 [1991].

Miyashita and Reed, "Bcl–2 Oncoprotein Blocks Chemotherapy–Induced Apoptosis in a Human Leukemia Cell Line," *Blood* 81:151–157 [1993].

Mizushima and Nagata, "pEF–BOS, a powerful mammalian expression vector," *Nucl. Acids Res.* 18:5322 [1990].

Montminy et al., "Identification of a cyclic–AMP–responsive element within the rat somatostatin gene," *Proc. Nal. Acad. Sci.* 83:6682–6686 [1996].

Nilsson et al., "Characterization of a Nuclear Factor That Binds Juxtaposed with AFT3/Jun on an Composite Response Element Specifically Mediating Induced Transcription in Response to an Epidermal Growth Factor/Ras/Raf Signaling Pathway," *Cell Growth & Differentation* 8:913–920 [1997].

Oberhammer et al., "Induction of apoptosis in cultured hepatocytes and in regressing liver by transforming growth factor β1," *Proc. Natl. Acad. Sci.* 89:5408–5412 [1992].

Panayotaos and Fontaine, "A Native Cruciform DNA Structure Probed in Bacteria by Recombinant T7 Endonuclease," *J. Biol. Chem.* 262:11364–13368 [1987].

Panayotatos and Wells, "Cruciform structures in supercoiled DNA," *Nature* 289:466–470 [1981].

Robertson et al., "Germ–line transmission of genes introduced into cultured pluripotential cells by retroviral vector," *Nature* 322:445–448 [1986].

Roesler et al., "Cyclic AMP and the Induction of Eukryotic Gene Transcription," *J. Biol. Chem.* 263:9063–9066 [1988].

Roush, "Antisense Aims for a Renaissance," *Science* 276:1192–1193 [1997].

Sambrook et al., *Molecular Cloning: A Laboratory Manual*, 2nd ed., Cold Spring Harbor Laboratory Press, New York [1989], pp. 7.39–7.52, 9.31–9.58, 16.7–16.15.

Short et al., "Characterization of the Phospheoenlpyruvate Carboxykinase (GTP) Promoter–regulatory Region," *J. Biol. Chem.* 261:9721–9726 [1986].

Stewart et al., "Expression of retroviral vectors in transgenic mice obtained by embryo infection," *EMBO J.*6:383–388 [1987].

Tsukada et al., "Identification of a Region in the Human Vasoactive Intestinal Polypeptide Gene Responsible for Regulation by Cyclic AMP," *J. Biol. Chem.* 262:8743–8747 [1987].

Uetsuki et al., "Isolation and Characterization of the Human Chromosomal Gene for Polypeptide Chain Elongation Factor–1α," *J. Biol. Chem.* 264:5791–5798 [1989].

Van der Putten et al., "Efficient insertion of genes into the mouse germ line via retroviral vectors," *Proc. Natl. Acad. Sci. USA* 82:6148–6152 [1985].

Van Beveren et al., "Analysis of FBJ–MuSV Provirus and c–fos (Mouse) Gene Reveals That Viral and Cellular for Gene Products Have Different Carboxy Termini," *Cell* 32:1241–1255 [1983].

Vaux et al., "Bcl–2 gene promotes haemopoietic cell survival and cooperates with c–myc to immortalize pre–B cells," *Nature* 335:440–442 [1988].

Verma and Somia, "Gene therapy—promises, problems and prospects," *Nature* 389:239–242 [1997].

Voss et al., "The role of enhancers in the regulation of cell–type–specific transcriptional control," *Trends Biochem. Sci.* 11:287–289 [1986].

Walton et al., "A Dominant Repressor of Cyclic Adenosine 3',5'–Monophosphate (cAMP)–Regulated Enhancer–Binding Protein Activity Inhibits the cAMP–Mediated Induction of the Somatostatin Promoter *in Vivo,*" *Mol. Endocrinol.* 6:647–655 [1992].

Wang and Calame, "SV40 Enhancer–Binding Factors Are Required at the Establishment but Not the Maintenance Step of Enhancer–Dependent Transcriptional Activation," *Cell* 47:241–247 [1986].

Wieland and Faulstich, "Amatoxins, Phallotoxins, Phallolysin, and Antamanide: The Biologically Active Components of Poisonous *Amanita* Mushrooms," *Crit. Rev. Biochem.* 5:185–260 [1978].

Williams and Andrisani, "The hepatitis B virus X protein targets the basic region–leucine zipper domain of CREB," *Proc. Natl. Acad. Sci.* 92:3819–3823 [1995].

Wu and Wallace, "The Ligation Amplification Reaction (LAR)—Amplification of Specific DNA Sequences Using Sequential Rounds of Template–Dependent Ligation," *Genomics* 4:560–569 [1989].

Zon, "Oligonucleotide Analogues as Potential Chemotherapeutic Agens," *Pharm. Res.* 5, 539 [1988].

Morishita et al., "A gene therapy strategy using a transcription factor decoy of the E2F binding site inhibits smooth muscle proliferation in vivo," *Proc. Natl. Acad. Sci. USA* 92:5855–5859 [1995].

Arias et al., "Activation of cAMP and mitogen responsive genes relies on a common nuclear factor," *Nature* 370:226 [1994].

Bantignies et al., "Genetic Characterization of Transactivation of the Human T–Cell Leukemia Virus Type 1 Promoter: Binding of Tax to Tax–Responsive Element 1 is Mediated by the Cyclic AMP–Responsive Members of the CREB/ATF Family of Transcription Factors," *Molecular and Cellular Biology* 16:2174–21182 [1996].

Benbrook and Jones, "Heterodimer formation between CREB and JUN proteins," *Oncogene* 5:295–302 [1990].

Bianchi et al., "Specific Recognition of Cruciform DNA by Nuclear Protein HMG1," *Science* 243:1056–1059 [1989].

Fazia et al., "Cyclic AMP Signalling and Cellular Proliferation: regulation of CREB and CREM," *FEBS letters* 410:22–24 [1997].

Ginty et al., "Nerve Growth Factor Activates a Ras–Dependent Protein Kinase That Stimulates c–fos Transcription via Phosphorylation of CREB," *Cell* 77:713–725 [1994].

Ji et al, "CREB Proteins Function as Positive Regulators of the Translocated bcl–2 Allele in t(14;18) Lymphomas," *Journal of Biological Chemistry* 271:22687–22691 [1996].

Kwok et al., "Nuclear protein CBP is a coactivator for the transcription factor CREB," *Nature* 370:223 [1994].

Montminy and Bilezikjian, "Binding of a nuclear protein to the cyclic–AMP response element of the somatostatin gene," *Nature* 328:175–178 [1987].

Neumann et al., "RelA/p65 is a molecular target for the immunosuppressive action of protein kinase A," *The EMBO Journal* 14:1991 [1995].

O'Brien et al., "Potential Convergence of Insulin and cAMP Signal Transduction Systems at the Phosphoenolpyruvate Carboxykinase (PEPCK) Gene Promoter through CCAAT/Enhancer Binding Protein (C/EBP)," *Journal of Biological Chemistry* 269:30419–30425 [1994].

Pittman et al., "Transcription of Cystic Fibrosis Transmembrane Conductance Regulator Requires a CCAAT–like Element for both Basal and cAMP–mediated Regulation," *J. Biol. Chem.* 270:28848–28857 [1995].

Riccio et al., "An NGF–TrkA–Mediated Retrograde Signal to Transcription Factor CREB in Sympathetic Neurons," *Science* 277:1097–1100 [1997].

Sonnenberg et al., "Regulation of Proenkephalin by Fos and Jun," *Science* 246:1622–1625 [1989].

Struthers et al., "Somatotroph hypoplasia and dwarfism in transgenic mice expressing a non–phosphorylatable CREB mutant," *Nature* 350:622–624 [1991].

Xing et al., "Coupling of the RAS–MAPK Pathway to Gene Activation by RSK2, a Growth Factor–Regulated CREB Kinase," *Science* 273:959–963 [1996].

TRANSCRIPTION FACTOR DECOY AND TUMOR GROWTH INHIBITOR

FIELD OF THE INVENTION

The present invention provides methods and compositions relating to oligonucleotides, with high affinity for a target transcription factor, that can be introduced into cells as decoy cis-elements to bind the factor and alter gene expression.

BACKGROUND OF THE INVENTION

A major focus of cellular and molecular research has concentrated on developing means to regulate gene expression (i.e., gene transcription and translation) in an effort to treat and cure a variety of disease and conditions. It is hoped that the up- or down-regulation of specific genes will alter or circumvent the molecular mechanisms underlying these diseases and conditions. The importance of such research has dramatically increased as the Human Genome Project continues to identify genes at an accelerated pace. Gene identification alone, however, is only a preliminary step towards gaining control over the associated diseases and conditions. Methods to manipulate the expression of these newly identified genes are needed as well.

Currently, several general methods have been developed to regulate and control gene expression at either the transcriptional or translational steps. Each of these methods suffers from significant drawbacks.

A. Global Transcription and Translation Regulators

One means of regulating gene expression is to use chemicals that alter the expression of all genes within a cell, tissue, or organism. For example, cycloheximide blocks the peptidyl transferase reaction on eukaryotic ribosomes and acts as a general inhibitor of translation (i.e., the translation of all genes within treated cells is inhibited). Likewise, α-amantin globally blocks mRNA synthesis by binding to eukaryotic RNA polymerase II. Furthermore, actinomycin D is capable of blocking RNA synthesis by intercalating into guanine-cytosine base pairs and disrupting transcription; netropsin and distamycin A block transcription by binding to DNA and blocking RNA polymerase; and acridines, such as proflavine, inhibit RNA synthesis by blocking the formation of the DNA/RNA polymerase complex. Because these chemicals prevent the expression of all genes, any prolonged treatment results in the loss of critical factors needed to maintain the cells, leading to irreparable damage or cell death (e.g., α-amantin was originally identified as a potent poison from the mushroom *Amanita phalloides;* Wieland and Faulstich, Crit. Rev. B. 5: 185 [1978]). To overcome these drawbacks, methods of regulating the expression of specific genes or gene families must be developed.

B. Regulation of Signal Transduction Pathways

One means of regulating gene expression is to activate or repress the signal transduction pathways that are responsible for regulating gene transcription. By activating or inhibiting important steps in the pathways (e.g., binding of signalling molecules to receptors, entry of signalling molecules into cells or nuclei, covalent modification of enzymes, or release or sequestration of ions from organelles), gene expression can be activated or repressed. For example, pain relievers such as aspirin and ibuprofen inhibit the enzymatic production of prostaglandins and result in decreased swelling and inflammation brought about by the signalling pathways normally initiated by the prostaglandins.

Unfortunately, the regulation of signal transduction pathways is not a viable means of treating many diseases and conditions. Most pathways have not been sufficiently characterized to rationally develop means of regulating expression and treating disease while avoiding unwanted side-effects. For example, many signal transduction pathways regulate a variety of genes in a variety of different cell types. Thus, in an attempt to shut off a gene responsible for a given disease, the pathway may also down-regulate other genes responsible for critical metabolic processes in the cells. Also, many signalling pathways are redundant (i.e., more than one pathway controls the down-stream regulatory event). Thus, by activating or repressing one pathway, another may compensate and confound the attempt at controlling gene expression. Furthermore, many signal transduction pathways cross-talk (i.e., share similar components and co-regulate one another). Thus the regulation of one pathway may result in the undesired regulation of other known, and yet unidentified, pathways. By inhibiting or activating a given step within a pathway, a range of known or unknown side-effects can occur. For example, prostaglandin signalling is involved not only in inflammatory responses, but is also believed to be involved in platelet aggregation, the sleep-wake cycle, some aspects of vision, luteolysis, and any number of yet unidentified physiological effects. Thus, in general, the regulation of signal transduction pathways provides a too broad and unpredictable means for controlling gene expression.

C. Gene Therapy

With the development of gene therapy techniques, it has become possible to replace or insert genes of interest into organisms. In theory, overactively expressed or mutated genes can be replaced by "normal" copies. Also, genes can be linked to controllable promoter elements (i.e., a promoter that can be turned on or off by administration of appropriate signalling compounds) and can be placed into target cells. For example, the gene for a desired transcription factor could be placed under the control of such an inducible/ repressible promoter. Using this technique, gene families that are activated or repressed by the transcription factor can be coordinately regulated by the administration of the appropriate signalling compounds. These transcription factors can be wild-type (i.e., to directly activate or repress a gene), mutants with DNA binding capability but altered active sites (i.e., to compete with the cell's natural transcription factors for binding to gene enhancers), or mutants with wild-type heterodimerization domains but altered active sites or DNA binding sites (i.e., to bind to the cell's natural transcription factors and prevent it from binding to enhancers and regulating gene expression).

Unfortunately, gene therapy techniques, as described above, are only in their initial stages of development. There are still significant problems to overcome, such as the lack of efficient delivery systems, lack of sustained expression, and host immune reactions (Verma and Somia, Nature 389, 239 [1997]). Even if these technologies eventually become widely available, they will be extremely complex, time-consuming, and unpredictable.

The art remains in need of means for regulating gene expression to control and treat human diseases such as cancer and viral infections. Such an approach should repress or activate specific genes or gene families without producing harmful side effects.

SUMMARY OF THE INVENTION

The present invention provides methods and compositions relating to oligonucleotides, with high affinity for a target transcription factor, that can be introduced into cells as decoy cis-elements to bind the factor and alter gene expression.

In one embodiment, the present invention provides a composition comprising one or more purified nucleic acid molecules that compete with cAMP response element (CRE) enhancer DNA for binding to one or more transcription factors. In some embodiments the nucleic acid molecules comprise DNA, although all nucleic acid molecules (e.g., RNA) are contemplated by the presently claimed invention.

In some embodiments the nucleic acid molecules comprise one or more single-stranded oligonucleotides that will hybridize to form a duplex. In preferred embodiments, the single-stranded oligonucleotides comprise one or more palindromic sequences. In particularly preferred embodiments, the single-stranded oligonucleotides comprise SEQ ID NO:2. However, all single-stranded oligonucleotide or oligonucleotides that can compete with cAMP response element (CRE) enhancer DNA for binding to one or more transcription factors are contemplated by the presently claimed invention.

In other embodiments, the nucleic acid molecules comprise one or more hairpin-forming single-stranded oligonucleotides. In preferred embodiments, the hairpin-forming single-stranded oligonucleotides comprise SEQ ID NO:3. In other embodiments, the nucleic acid molecule comprises two hairpin-forming oligonucleotides complementary to one another in a manner wherein combining the two hairpin-forming oligonucleotides produces a cruciform structure. In some embodiments, these two hairpin forming oligonucleotides comprise SEQ ID NO:10 and SEQ ID NO:11.

Although not required by the presently claimed invention, in some embodiments the nucleic acid molecules contain modified phosphodiester bonds. In some embodiments, these modified phosphodiester bonds are selected from the group consisting of phosphorothioate, phosphoramidite, and methyl phosphate derivatives.

The presently claimed invention provides a method for regulating gene transcription in target cells comprising: providing one or more cAMP response element decoys and one or more target cells containing cAMP response element enhancer DNA and one or more transcription factors that associate with the cAMP response element enhancer DNA; and exposing the target cells to the cAMP response element decoys under condition such that the cAMP response element decoys will compete with the cAMP response element enhancer DNA for binding to the one or more transcription factors.

In some embodiments of this method, the cAMP response element decoys comprise DNA, although all nucleic acid (e.g., RNA) molecules are contemplated by the presently claimed invention. In other embodiments the cAMP response element decoys comprise one or more single-stranded oligonucleotides that will hybridize to form a duplex. In preferred embodiments, the single-stranded oligonucleotides comprise one or more palindromic sequences. In particularly preferred embodiments, the single-stranded oligonucleotides comprise SEQ ID NO:2. However, all single-stranded oligonucleotide or oligonucleotides that can compete with cAMP response element (CRE) enhancer DNA for binding to one or more transcription factors are contemplated by the presently claimed invention.

In other embodiments of this method, the cAMP response element decoys comprise one or more hairpin-forming single-stranded oligonucleotides. In preferred embodiments, the hairpin-forming single-stranded oligonucleotides comprise SEQ ID NO:3. In other embodiments, the cAMP response element decoys comprises two hairpin-forming oligonucleotides complementary to one another in a manner wherein combining the two hairpin-forming oligonucleotides produces a cruciform structure. In some embodiments, these two hairpin forming oligonucleotides comprise SEQ ID NO:10 and SEQ ID NO:11.

Although not required by the presently claimed invention, in some embodiments the cAMP response element decoys contain modified phosphodiester bonds. In some embodiments, these modified phosphodiester bonds are selected from the group consisting of phosphorothioate, phosphoramidite, and methyl phosphate derivatives.

In certain embodiments of the presently claimed method, the target cells comprise cancer cells.

In some embodiments, the method of exposing of the target cells to the cAMP response element decoys is selected from the group consisting of injection, direct exposure, oral intake, transfection, and transgenic expression, although all methods of exposure are contemplated by the presently claimed invention.

The presently claimed invention further provides methods for regulating cancer cell proliferation in vivo comprising: providing one or more cAMP response element decoys and one or more target cells containing cAMP response element enhancer DNA and one or more transcription factors that associate with the cAMP response element enhancer DNA; and exposing the target cells to the cAMP response element decoys under condition such that the cAMP response element decoys will compete with the cAMP response element enhancer DNA for binding to the one or more transcription factors.

In some embodiments of this method, the cAMP response element decoys comprise DNA, although all nucleic acid molecules are contemplated by the presently claimed invention. In other embodiments the cAMP response element decoys comprise one or more single-stranded oligonucleotides that will hybridize to form a duplex. In preferred embodiments, the single-stranded oligonucleotides comprise one or more palindromic sequences. In particularly preferred embodiments, the single-stranded oligonucleotides comprise SEQ ID NO:2. However, all single-stranded oligonucleotide or oligonucleotides that can compete with cAMP response element (CRE) enhancer DNA for binding to one or more transcription factors are contemplated by the presently claimed invention.

In other embodiments of this method, the cAMP response element decoys comprise one or more hairpin-forming single-stranded oligonucleotides. In preferred embodiments, the hairpin-forming single-stranded oligonucleotides comprise SEQ ID NO:3. In other embodiments, the cAMP response element decoys comprises two hairpin-forming oligonucleotides complementary to one another in a manner wherein combining the two hairpin-forming oligonucleotides produces a cruciform structure. In some embodiments, these two hairpin forming oligonucleotides comprise SEQ ID NO:10 and SEQ ID NO:11.

Although not required by the presently claimed invention, in some embodiments the cAMP response element decoys contain modified phosphodiester bonds. In some embodiments, these modified phosphodiester bonds are selected from the group consisting of phosphorothioate, phosphoramidite, and methyl phosphate derivatives.

In some embodiments, the method of exposing of the target cells to the cAMP response element decoys is selected from the group consisting of injection, direct exposure, oral intake, transfection, and transgenic expression, although all methods of exposure are contemplated by the presently claimed invention.

DEFINITIONS

Figure 1:
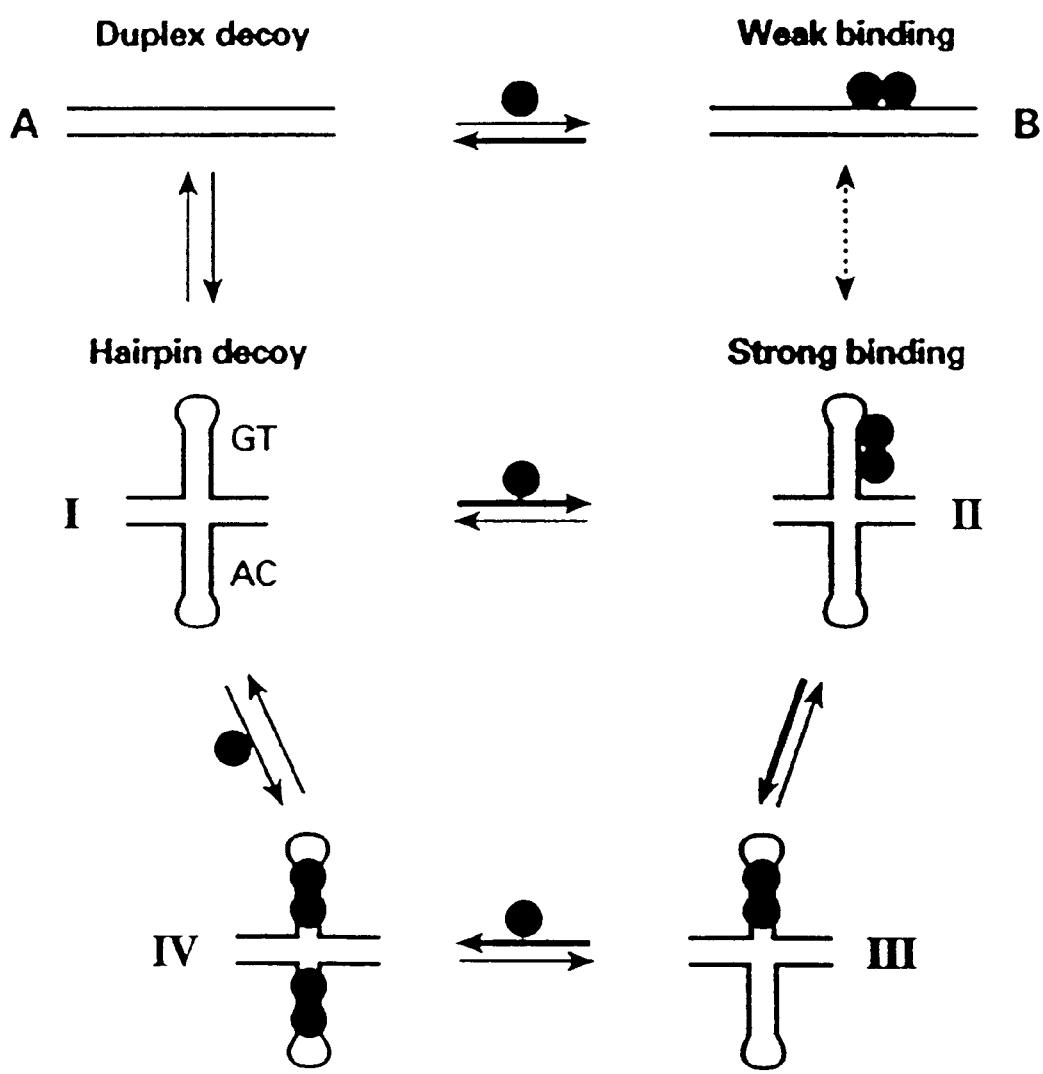
FIG. 1 is a schematic diagram showing the transitions and binding affinities of transcription factors to linear duplex and hairpin cruciform oligonucleotides.

To facilitate an understanding of the invention, a number of terms are defined below.

The term "biologically active," as used herein, refers to a protein or other biologically active molecules (e.g., catalytic RNA) having structural, regulatory, or biochemical functions of a naturally occurring molecule.

The term "agonist," as used herein, refers to a molecule which, when interacting with an biologically active molecule, causes a change (e.g., enhancement) in the biologically active molecule, which modulates the activity of the biologically active molecule. Agonists may include proteins, nucleic acids, carbohydrates, or any other molecules which bind or interact with biologically active molecules. For example, agonist can alter the activity of gene transcription by interacting with RNA polymerase directly or through a transcription factor.

The terms "antagonist" or "inhibitor," as used herein, refer to a molecule which, when interacting with a biologically active molecule, blocks or modulates the biological activity of the biologically active molecule. Antagonists and inhibitors may include proteins, nucleic acids, carbohydrates, or any other molecules which bind or interact with biologically active molecules. Inhibitors and antagonists can effect the biology of entire cells, organs, or organisms (e.g., an inhibitor that slows tumor growth).

The term "modulate," as used herein, refers to a change or an alteration in the biological activity of a biologically active molecule. Modulation may be an increase or a decrease in activity, a change in binding characteristics, or any other change in the biological, functional, or immunological properties of biologically active molecules.

As used herein, the term "nucleic acid molecule" refers to any nucleic acid containing molecule including, but not limited to DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide or precursor (e.g., c-myc). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb or more on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Upregulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

As used herein, the term "pleiotropic activator" refers to activators that function on a multiplicity of different genes and have a multiplicity of different effects.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence which encodes a gene product. The coding region may be present in either a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 100 residues long (e.g., between 15 and 50), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the term "transcription factor" refers to proteins that interact with one another and RNA polymerase enzyme to modulate transcription. Transcription factors target genes by recognizing specific DNA regulatory sequences (e.g., enhancers) or other transcription factors. Transcription factors are often referred to as "trans-factors" that interact with "cis-elements" (e.g., enhancers) because they are typically produced from genes located distantly (trans) from their sites of regulation (cis). Some transcription factors are biologically active only when bound to another copy of itself (i.e., homodimers linked through "homodimerization domains") or to other transcription factors (i.e., heterodimers linked through "heterodimerization domains"). For most transcription factors, specific and distinct regions of the protein mediate DNA binding (i.e., "tDNA binding domains") and transcriptional activation (i.e., "activation domains"). The term "CRE transcription factor" refers to transcription factors (e.g., peptides) that recognize and bind to cAMP response elements (i.e., "cAMP response element enhancer DNA") or to proteins bound to such elements. This term encompasses both identified (e.g., CREB) and yet unidentified transcription factors.

As used herein, the term "trans-dominant mutant" refers to transcription factors that compete with wild-type transcription factors (i.e., "transactivators") for binding to enhancer sequences.

As used herein, the terms "decoy" and "transcription factor decoy" refer to molecules that bind to or interact with transcription factors and prevent their binding to native enhancer sequences. Decoys include nucleic acid sequences, including, but not limited to, oligonucleotides that correspond to (i.e., are identical to or essentially identical to) the native enhancer. Such oligonucleotides include, but are not limited to, single stranded palindromic oligonucleotides comprising one or more repeats of the enhancer sequence, sense and antisense oligonucleotides comprising one or more repeats of the enhancer sequence, oligonucleotides that form hairpin structures such that a duplex binding site for the transcription factor is generated, and one or more oligonucleotides that form a cruciform structure such that one or more binding sites for the transcription factor are generated. The terms "CRE transcription factor decoy" and "cAMP response element decoy" refer to decoys that target transcription factors associated with cAMP response elements.

As used herein, the term "duplex," in reference to oligonucleotides, refers to regions that are double stranded through hybridization of complementary base pairs. The term "hairpin" refers to double-stranded nucleic acid structures formed by base-pairing between regions of the same strand of a nucleic acid molecule. The regions are arranged inversely and can be adjacent or separated by noncomplementary sequence (i.e., thus forming a loop structure or "stem-loop"). The term "cruciform" refers to structures formed in double-stranded nucleic acids by inverted repeats separated by a short sequence. Cruciform structures can be generated through the hybridization of two or more hairpin structures where the hairpin duplex and loop comprise the short sequence separating the inverted repeats. Cruciform structures can comprise one or more nucleic acid molecules.

As used herein, the term "palindrome" refers to regions of nucleic acid in which the sequence of both strands is identical when read in antiparallel directions (i.e., both strands read 5' to 3' or 3' to 5').

As used herein, the term "high affinity" refers to the non-random interaction of a molecule with itself or another molecule. Molecules with affinity for one another will tend to "bind" (i.e., chemically associate through weak or strong chemical interactions) and form a stable complex. For example, a transcription factor will have high affinity for polynucleotide sequences that correspond to its DNA binding domain and low affinity for other nucleic acid sequences.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. (defined infra).

Transcriptional control signals in eukaryotes comprise "promoter" and "enhancer" elements. Promoters and enhancers consist of short arrays of DNA sequences that interact specifically with cellular proteins involved in transcription (T. Maniatis et al., Science 236:1237 [1987]). Promoter and enhancer elements have been isolated from a variety of eukaryotic sources including genes in yeast, insect and mammalian cells and viruses (analogous control elements, i.e., promoters, are also found in prokaryote). The selection of a particular promoter and enhancer depends on what cell type is to be used to express the protein of interest. Some eukaryotic promoters and enhancers have a broad host range while others are functional in a limited subset of cell types (for review see, S. D. Voss et al., Trends Biochem. Sci., 11:287 [1986]; and T. Maniatis et al., supra). For example, the SV40 early gene enhancer is very active in a wide variety of cell types from many mammalian species and has been widely used for the expression of proteins in mammalian cells (R. Dijkema et al., EMBO J. 4:761 [1985]). Two other examples of promoter/enhancer elements active in a broad range of mammalian cell types are those from the human elongation factor 1α gene (T. Uetsuki et al., J. Biol. Chem., 264:5791 [1989]; D. W. Kim et al., Gene 91:217 [1990]; and S. Mizushima and S. Nagata, Nuc. Acids. Res., 18:5322 [1990]) and the long terminal repeats of the Rous sarcoma virus (C. M. Gorman et al., Proc. Natl. Acad. Sci. USA 79:6777 [1982]) and the human cytomegalovirus (M. Boshart et al., Cell 41:521 [1985]).

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

As used herein, the term "cAMP response element" or "CRE" refers to enhancer sequences that interact with transcription factors which mediate signal transduction involving cAMP. A consensus sequence has been described for CRE enhancers, comprising 5'-TGACGTCA-3' (SEQ ID NO:1). However, CREs from many genes that deviate from this sequence have been identified (Roesler et al., supra). Such sequences include, but are not limited to, TTACGTCA (SEQ ID NO:4) (Short et al., J. Biol. Chem. 261, 9721 [1986]), TGACGTCT (SEQ ID NO:5) (Tsukada et al., J. Biol. Chem. 262, 8743 [1987]), TGACGTAG (SEQ ID NO:6) (VanBeveren et al., Cell 32, 1241 [1983]), and CTGCGTCA (SEQ ID NO:7) (Comb et al., Nature 323, 353 [1986]). Genes that have CREs are referred to as "cAMP-sensitive genes."

As used herein, the term "Nucleic acid molecules that compete with response element enhancer DNA for binding to transcription factors" refers to any nucleic acid molecule with affinity for a transcription factor DNA binding site or otherwise interacts with the transcription factor to prevent or reduce binding to native enhancer sequences. Thus, such molecules are defined functionally, rather than strictly structurally. In this regard, such functionality is readily testable in the assays described herein. Specifically, the assay described in Example 1 below provides a convenient test format for screening candidate molecules and thereby identifying competing molecules. Additionally, there are a variety of computer programs and services available for comparing sequence and structural information about oligonucleotides that may be used to identify candidates for submitting to the functional screening methods described in Example 1. Such candidate molecules typically comprise one or more duplex portions, including but not limited to linear duplex, hairpin, and cruciform structures. These molecules can comprise the consensus sequence for a given transcription factor (e.g., the CRE consensus sequence 5'-TGACGTCA-3'). Additionally, molecules similar to the consensus sequence (i.e., molecules that have one or a few base substitutions, deletions, or additions from the known response element and that retain their palindromic or secondary structural characteristics) can provide effective decoys, with potency varying by gene, cell type, and species (e.g., duplex forming oligonucleotides that are sufficiently similar in sequence to the consensus sequence or any known response element can be used as decoys). However, regardless of sequence, any oligonucleotide that contains sufficient structure to exhibit affinity for the DNA binding site of the targeted transcription factor will find use with, and is contemplated by, the present invention.

As used herein, the term "CRE-transcription factor complex" refers to the collection of proteins (e.g., transcription factors) involved in regulating gene expression through a cAMP response element. Such proteins include known factors (e.g., CREB) and yet unidentified factors.

The presence of "splicing signals" on an expression vector often results in higher levels of expression of the recombinant transcript. Splicing signals mediate the removal of introns from the primary RNA transcript and consist of a splice donor and acceptor site (J. Sambrook el al., *Molecular Cloning: A Laboratory Manual,* 2nd ed., Cold Spring Harbor Laboratory Press, New York [1989], pp. 16.7–16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (J. Sambrook, supra, at 16.6–16.7).

Eukaryotic expression vectors may also contain "viral replicons" or "viral origins of replication." Viral replicons are viral DNA sequences which allow for the extrachromosomal replication of a vector in a host cell expressing the appropriate replication factors. Vectors which contain either the SV40 or polyoma virus origin of replication replicate to high "copy number" (up to $10^4$ copies/cell) in cells that express the appropriate viral T antigen. Vectors which contain the replicons from bovine papillomavirus or Epstein-Barr virus replicate extrachromosomally at "low copy number" (~100 copies/cell).

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids'bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions which promote hybridization under conditions of high stringency (e.g., increasing the temperature of the hybridization and/or wash steps, the use of formamide in the hybridization solution, etc.) (see definition below for "stringency").

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described above.

A gene may produce multiple RNA species which are generated by differential splicing of the primary RNA transcript. cDNAs that are splice variants of the same gene will contain regions of sequence identity or complete homology (representing the presence of the same exon or portion of the same exon on both cDNAs) and regions of complete nonidentity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe which can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m = 81.5 + 0.41(\% \text{ G+C})$, when a nucleic acid is in aqueous solution at 1 M NaCl (See e.g. Anderson and Young, Quantitative Filter Hybridization, in *Nucleic Acid Hybridization* [1985]). Other references include more sophisticated computations which take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (D. L. Kacian et al., Proc. Natl. Acad. Sci. USA 69:3038 [1972]). Other nucleic acid will not be replicated by this amplification enzyme. Similarly, in the case of T7 RNA polymerase, this amplification enzyme has a stringent specificity for its own promoters (M. Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (D. Y. Wu and R. B. Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press [1989]).

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of "target" (defined below). In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," refers to the region of nucleic acid bounded by the primers. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the term "RT-PCR" refers to the replication and amplification of RNA sequences. In this method, reverse transcription is coupled to PCR, most often using a one enzyme procedure in which a thermostable polymerase is employed, as described in U.S. Pat. No. 5,322,770, herein incorporated by reference. In RT-PCR, the RNA template is converted to cDNA due to the reverse transcriptase activity of the polymerase, and then amplified using the polymerizing activity of the polymerase (i.e., as in other PCR methods).

As used herein, the terms "restriction endonucleases" and "restriction enzymes" refer to bacterial enzymes, each of which cut double-stranded DNA at or near a specific nucleotide sequence.

As used herein, the term "antisense" is used in reference to DNA or RNA sequences which are complementary to a specific DNA or RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter which permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (–) (i.e., "negative") is sometimes used in reference to the antisense strand, with the designation (+) sometimes used in reference to the sense (i.e., "positive") strand.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNA s which encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and antisense strands (i.e., the oligonucleotide or polynucleotide may be double-stranded).

As used herein, a "portion of a chromosome" refers to a discrete section of the chromosome. Chromosomes are divided into sites or sections by cytogeneticists as follows: the short (relative to the centromere) arm of a chromosome is termed the "p" arm; the long arm is termed the "q" arm. Each arm is then divided into 2 regions termed region 1 and region 2 (region 1 is closest to the centromere). Each region is further divided into bands. The bands may be further divided into sub-bands. For example, the 11p15.5 portion of human chromosome 11 is the portion located on chromosome 11 (11) on the short arm (p) in the first region (1) in the 5th band (5) in sub-band 5 (0.5). A portion of a chromosome may be "altered;" for instance the entire portion may be absent due to a deletion or may be rearranged (e.g., inversions, translocations, expanded or contracted due to changes in repeat regions). In the case of a deletion, an attempt to hybridize (i.e., specifically bind) a probe homologous to a particular portion of a chromosome could result in a negative result (i.e., the probe could not bind to the sample containing genetic material suspected of containing the missing portion of the chromosome). Thus, hybridization of a probe homologous to a particular portion of a chromosome may be used to detect alterations in a portion of a chromosome.

The term "sequences associated with a chromosome" means preparations of chromosomes (e.g., spreads of metaphase chromosomes), nucleic acid extracted from a sample containing chromosomal DNA (e.g., preparations of genomic DNA); the RNA which is produced by transcription of genes located on a chromosome (e.g., hnRNA and mRNA) and cDNA copies of the RNA transcribed from the DNA located on a chromosome. Sequences associated with a chromosome may be detected by numerous techniques including probing of Southern and Northern blots and in situ hybridization to RNA, DNA or metaphase chromosomes with probes containing sequences homologous to the nucleic acids in the above listed preparations.

As used herein the term "coding region" when used in reference to structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

As used herein, the term "structural gene" refers to a DNA sequence coding for RNA or a protein. In contrast, "regulatory genes" are structural genes which encode products which control the expression of other genes (e.g., transcription factors).

As used herein, the term "purified" or "to purify" refers to the removal of contaminants from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook el al., *Molecular Cloning: A Laboratory Manual,* Cold Spring Harbor Press, NY, pp 9.31–9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, J. et al., supra, pp 7.39–7.52 [1989]).

The term "Western blot" refers to the analysis of protein (s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabelled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labelled "A" and the antibody will reduce the amount of labelled A bound to the antibody.

The term "transgene" as used herein refers to a foreign gene that is placed into an organism by introducing the foreign gene into newly fertilized eggs or early embryos. The term "foreign gene" refers to any nucleic acid (e.g., gene sequence) which is introduced into the genome of an animal by experimental manipulations and may include gene sequences found in that animal so long as the introduced gene does not reside in the same location as does the naturally-occurring gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Embryonal cells at various developmental stages can be used to introduce transgenes for the production of transgenic animals, often referred to as "gene therapy." Different methods are used depending on the stage of development of the embryonal cell. The zygote is the best target for micro-injection. In the mouse, the male pronucleus reaches the size of approximately 20 micrometers in diameter which allows reproducible injection of 1–2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438–4442 [1985]). As a consequence, all cells of the transgenic animal will carry the incorporated transgene. This will in general also be reflected in the efficient transmission of the transgene to offspring of the founder since 50% of the germ cells will harbor the transgene. Micro-injection of zygotes is the preferred method for incorporating transgenes in practicing the invention. U.S. Pat. No. 4,873,191 describes a method for the micro-injection of zygotes; the disclosure of this patent is incorporated herein in its entirety.

Retroviral infection can also be used to introduce transgenes into animals. The developing embryo can be cultured in vitro to the blastocyst stage. During this time, the blastomeres can be targets for retroviral infection (Janenich, Proc. Natl. Acad. Sci. USA 73:1260–1264 [1976]). Efficient infection of the blastomeres is obtained by enzymatic treatment to remove the zona pellucida (Hogan et al., in *Manipulating the Mouse Embryo,* Cold Spring Harbor Laboratory Press, Cold Spring Harbor, N.Y. [1986]). The viral vector system used to introduce the transgene is typically a replication-defective retrovirus carrying the transgene (D. Jahner et al., Proc. Natl. Acad Sci. USA 82:6927–693 [1985]). Transfection is easily and efficiently obtained by culturing the blastomeres on a monolayer of virus-producing cells (Van der Putten, supra; Stewart, et al., EMBO J. 6:383–388 [1987]). Alternatively, infection can be performed at a later stage. Virus or virus-producing cells can be injected into the blastocoele (D. Jahner el al., Nature 298:623–628 [1982]). Most of the founders will be mosaic for the transgene since incorporation occurs only in a subset of cells which form the transgenic animal. Further, the founder may contain various retroviral insertions of the transgene at different positions in the genome which generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involves the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

A third type of target cell for transgene introduction is the embryonal stem (ES) cell. ES cells are obtained by culturing pre-implantation embryos in vitro under appropriate conditions (Evans et al., Nature 292:154–156 [1981]; Bradley et al., Nature 309:255–258 [1984]; Gossler et al., Proc. Acad. Sci. USA 83:9065–9069 [1986]; and Robertson et al., Nature 322:445–448 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468–1474 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells which have integrated the transgene. This technique obviates the need for growth of the transfected ES cells under appropriate selective conditions prior to transfer into the blastocoel.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell which has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells which have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

As used herein, the term "selectable marker" refers to the use of a gene which encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity which can be detected in any eukaryotic cell line. Examples of dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid. Other selectable markers are not dominant in that there use must be in conjunction with a cell line that lacks the relevant enzyme activity. Examples of non-dominant selectable markers include the thymidine kinase (tk) gene which is used in conjunction with tk⁻ cell lines, the CAD gene which is used in conjunction with CAD-deficient cells and the mammalian hypoxanthine-guanine phosphoribosyl transferase (hprt) gene which is used in conjunction with hprt⁻ cell lines. A review of the use of selectable markers in mammalian cell lines is provided in Sambrook, J. et al., *Molecular Cloning: A Laboratory Manual,* 2nd ed., Cold Spring Harbor Laboratory Press, New York (1989) pp.16.9–16.15.

As used herein, the term "signal transduction" refers to the process of transferring information from a chemical signal (e.g., a hormone, a growth factor, or neurotransmitter) into a cell and along an intracellular chain of signalling molecules (i.e., a "signal transduction pathway") to stimulate the appropriate cellular response (e.g., activation or repression of gene expression). For example, an extracellular signal can bind to a cell membrane receptor and activate the enzyme adenyl cyclase, leading to an increase in intracellular cAMP concentrations. The increase in cAMP concentrations can activate other intracellular proteins that can eventually lead to the binding of an active transcription factor to CRE elements and alter gene expression of CRE-sensitive genes.

As used herein, the term "intercalation" refers to the process of interposing or inserting something between two or more objects. For example, ethidium bromide can intercalate between nucleotides within a DNA molecule, while actinomycin D can intercalate between guanine-cytosine base pairs.

As used herein, the term "phosphodiester bond" refers to the covalent phosphate linkage between residues in a polynucleotide chain.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

As used herein, the term "differentiation" refers to the expression and manifestation of the fate of a cell. The term "apoptosis" refers to the programmed (i.e., genetically controlled) death of a cell. Apoptosis is characterized by loss of cell junctions, loss of micovilli, condensed cytoplasm, margination of nuclear chromatin into discrete masses, compacting of mitochondria and ribosomes, dilation of the endoplasmic reticulum, and break-up of cells into several membrane bound bodies (i.e., apoptotic bodies).

The term "test compound" refers to any chemical entity, pharmaceutical, drug, and the like that can be used to treat or prevent a disease, illness, sickness, or disorder of bodily function. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

A "composition comprising a given polynucleotide sequence" as used herein refers broadly to any composition containing the given polynucleotide sequence. The composition may comprise an aqueous solution. Compositions comprising polynucleotide sequences that are partially or completely complementary to an enhancer element (e.g., SEQ ID NO:1) may be employed as transcription factor decoys.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

DETAILED DESCRIPTION OF THE INVENTION

The present invention provides methods and compositions relating to oligonucleotides, with high affinity for a target transcription factor, that can be introduced into cells as decoy cis-elements to bind the factor and alter gene expression. Specifically, the present invention provides nucleic acid molecules that compete with cAMP response element (CRE) enhancers for binding to transcription factors. These nucleic acid molecules were shown to function in vitro and in vivo as inhibitors of tumor cell growth, without affecting the growth of non-cancerous cells. The present invention provides a powerful new means of combatting cancers by regulating the expression of cAMP-sensitive genes.

A. Enhancers and Transcription Factors

Eukaryotic transcription is regulated by the interplay of various protein factors at promoters (Maniatis el al., Science 236, 1237 [1987]). RNA polymerase binds to the promoter and catalyzes the synthesis of RNA from the DNA template. The binding of RNA polymerase and its activity can be regulated by the presence or absence of other protein regulators (i.e., transcription factors). Some transcription factors (e.g., activators or repressors) bind to specific DNA sequences called enhancers. Enhancer are typically located 5' of the gene they regulate, but can be found within the gene itself, 3' of the gene, distantly 5' of the gene, or even on other portions of the chromosome. Some transcription factors do not directly bind to enhancer sequences, but are associated with other proteins that do.

The displacement of transcription factors from their enhancer binding sites offers a means of regulating gene expression. For example, it has been shown that prokaryotic repressors can function as negative regulators of eukaryotic promoters (Hu and Davidson, Cell 53, 927 [1988]). This observation suggests that displacement of activating proteins might provide a general strategy for gene-specific repression in eukaryotes. Several approaches have been undertaken to control eukaryotic gene expression through such displacement, although none have found great success.

In one approach, trans-dominant mutants are generated that interfere with the function of transactivators. Mutants are generated that retain the ability to bind to cis-regulatory DNA sequences but that have dysfunctional transcriptional activation domains. These mutant transcription factors compete with their functional, wild-type counterparts for binding to the enhancer sequences and prevent the activation or repression or the target gene. While this strategy has been successful, in vitro (See e.g., Friedman et al., Nature 335: 452 [1988]), the generation of such mutants is not always possible. The transcription factor must be well characterized such that the activation domain(s) are identified and can be mutated. Also, even with sufficient knowledge to generate such mutants, time consuming, expensive, and difficult gene therapy procedures would be required to express these proteins in vivo.

In another approach, promoter competition is utilized whereby plasmids containing cis-acting elements, in common with the targeted gene, are introduced in high copy number into cells (Wang and Calame, Cell 47: 241 [1986]). At high copy number, a majority of the transcription factors can be competitively bound away from the natural enhancer sequences with gene expression accordingly regulated. Because these plasmids must be maintained uniformly in large numbers of cells, this approach has also been limiting.

Another approach used oligonucleotides to form triple helices with enhancer elements. Pyrimidine oligonucleotides were found to bind with sequence-specific dependence to homopurine sites in duplex DNA by triple helix formation and had sufficient specificity and affinity to compete with site-specific DNA binding proteins for occupancy of overlapping target sites (Maher III et al., Science 245, 725 [1989]). However, such oligonucleotide-directed triple helix formation has not been shown in cells in vitro or in vivo.

B. Competition with the CRE Enhancer

The approach of the presently claimed invention used oligonucleotides, modified to facilitate entry into cells, that compete with the native cellular cAMP response element (CRE) enhancers for binding to transcription factors. This decoy approach proved successful in vivo and in vitro in regulating gene expression.

The transcription factor decoys of the presently claimed invention are recognized and bound by transcription factors such that the factors can no longer bind to native response elements and regulate gene expression. Decoys can comprise one or more duplex nucleic acid structures. These structures are recognized by the DNA binding domain of the target transcription factors. The present invention is not intended to be limited to decoys with duplex structures however, as any nucleic acid structure that binds to the DNA binding domains is contemplated. The decoys can comprise the consensus sequence for the targeted transcription factor. A consensus sequence is identified as the sequence that, on average (i.e., in the most genes studied thus far or in binding affinity studies), binds with the highest affinity to its associated transcription factor(s). However, the decoys of the present invention are not limited to sequences comprising the consensus sequence. A variety of enhancers, with sequences slightly divergent from a consensus sequence, are often known to bind to the associated transcription factor. The present invention contemplates decoys comprising sequences from such known enhancers. The present invention further contemplates decoys comprising sequences similar to a consensus sequence and other known enhancers. Any decoy that has affinity for the target transcription factor(s) is suitable for use as a decoy and is contemplated by the presently claimed invention.

The CRE, 5'-TGACGTCA-3' (SEQ ID NO:1), has been described as the consensus sequence for the cis-element that directs cAMP-induced gene transcription (Roesler et al., J. Biol. Chem. 263, 9063 [1988]). The CRE-transcription factor complex is a pleiotropic activator that participates in the induction of a wide variety of cellular and viral genes. However, a CRE decoy oligonucleotide has never been described previously. It was not clear that such an oligonucleotide could be generated in a manner that would effectively compete with the natural CRE enhancers to regulate gene expression. Because the identity of the CRE transcription factor complex or complexes has not been thoroughly characterized, the effect of a given oligonucleotide decoy could not be predicted. For example, it is possible that sequences flanking the CRE enhancer are required for optimal transcriptional regulation by CRE transcription factors in a given gene. If these sequences are not included in the decoy oligonucleotide, the decoy may not effectively compete with the native enhancer for binding to the transcription factor complex. The exact sequence needed for any given gene may vary, making prediction impossible. Therefore, it was not predictable that CRE oligonucleotide decoys would work.

Furthermore, even if such a decoy oligonucleotide worked efficiently, it was not clear how the modification of transcription would affect the targeted cells. Because there are many cAMP-regulated genes and because they are ubiquitous in all cell types, it was feared that the use of CRE decoys would be detrimental to cells and organisms.

Surprisingly, the present invention demonstrated that duplex, hairpin, and cruciform oligonucleotides containing the core CRE consensus sequence (i.e., decoys), effectively regulated gene transcription in a wide variety of cell types. Even more surprisingly, the present invention demonstrated that cancer cell growth was inhibited by CRE decoy oligonucleotides, without adversely affecting non-cancerous cells.

The CRE decoy oligonucleotides of the present invention comprise sequences that contain one or more CRE binding sites. In some embodiments, the decoys comprise oligonucleotides containing the CRE consensus sequence (i.e., 5'-TGACGTCA-3'; SEQ ID NO:1), although any sequence with affinity for CRE transcription factors is contemplated by the present invention. Such sequences include, but are not limited to, TTACGTCA (SEQ ID NO:4) (Short et al., J. Biol. Chem. 261, 9721 [1986]), TGACGTCT (SEQ ID NO:5) (Tsukada et al., J. Biol. Chem. 262, 8743 [1987]), TGACG-TAG (SEQ ID NO:6) (VanBeveren et al., Cell 32, 1241 [1983]), CTGCGTCA (SEQ ID NO:7) (Comb et al., Nature 323, 353 [1986]), TGCGTCA (SEQ ID NO:13), and TGGCGTAG (SEQ ID NO: 14) (Kwast-Welfeld et al., Cellular and Molecular Biology Research 39, 231 [1993]). As is clear from these other enhancers, nucleic acid sequences with one or more bases different from the consensus sequence can still be recognized by the transcription factors. Thus a range of sequences can be effectively employed as decoys. By selecting sequences sufficiently divergent from the consensus sequence, decoys can be generated with varying affinities (i.e., potencies).

Furthermore, studies have shown that some cAMP-inducible gene promoters require an additional conserved sequence 3' of the CRE sequence for optimal binding and maximal responsiveness (Kwast-Welfeld et al., supra). Therefore, in some embodiments, the presently claimed invention contemplates the addition of one or more such flanking sequences 3' of the CRE element, if desired, to optimize decoy potency. Such flanking sequences are typically within six nucleotides of the core CRE and comprise sequences including, but not limited to, GAGA, GAAG, GAGG, GAGC, GGGAG, GGCC, GGAGC, GGGAA, CAGC, GCAG, AGAG, and GAGTA.

In some embodiments, the oligonucleotides of the present invention are synthesized with modified phosphodiester bonds, including, but not limited to phosphorothioate, phosphoramidite, or methyl phosphonate derivatives. However, the present invention is not limited to the use of oligonucleotides with modified phosphodiester bonds. The modified oligonucleotides can be synthesized in large amounts and are relatively resistant to nucleases (Zon, Pharm. Res. 5, 539 [1988]; and Agrawal et al., Proc. Natl. Acad. Sci. 85, 7079 [1988]). Because of their increased cell permeability and stability, such compounds have been used as mRNA antisense agents (Crooke, Annu. Rev. Pharmacol. Toxicol. 32, 329 [1992]; and Roush, Science 276, 1192 [1997]). However, unlike the mRNA antisense applications, the present invention takes advantage of these features to provide a means for directly targeting transcription factors rather than mRNA. Furthermore, the present invention provides novel methods and compositions for globally controlling the expression of genes that are regulated through CREs, unlike the antisense method, which only target mRNA for one specific gene product. Also, unlike the oligonucleotides of the present invention, mRNA antisense molecules sometimes trigger dangerous side-effects in animals such as extreme immune responses, blood clotting, cardiovascular problems, and even death (Gura, Science 270: 577 [1995]). Additionally, antisense molecules directed to mRNA require sequence knowledge of the gene to be regulated. In the presently claimed invention, only the sequence of the response element is needed (i.e., knowing the sequence of a response element allows for the regulation of both identified and unidentified genes that are transcriptionally regulated by the element).

In some embodiments of the present invention, the oligonucleotides were palindromic cis-transcription elements comprising a synthetic single-stranded oligonucleotide composed of the CRE cis-element that self-hybridized to form a duplex. When introduced into cells, these oligonucleotides acted as decoys for the CRE transcription factors and interfered with the cis-element-directed transcription. While the present invention is not limited to any particular mechanism, it is known that perfect palindromes are capable of forming strong hairpin structures. Such structures may be formed by the palindromic decoys, facilitating enhanced binding to the target transcription factors.

A similar approach can be used for a cis-element that is not palindromic. In this case, two synthetic single-stranded oligonucleotides, each composed of the sense- and antisense-cis-element, respectively, in combination can be used as the transcription factor decoy.

These single-stranded oligonucleotides can contain multiple copies of the cis-element. In one preferred embodiment, the CRE-palindrome comprises a triplet repeat of the CRE consensus sequence: 5'-TGACGTCATGACGTCATGACGTCA-3' (SEQ ID NO:2).

In other embodiments, synthetic oligonucleotides designed to form hairpin structures and comprising a cis-transcription element were used as transcription factor decoys. Recent evidence has indicated that DNA hairpin formation may represent an additional level of transcriptional control. For example, 23-bp synthetic oligonucleotide of human enkephalin gene enhancer has been shown to undergo a reversible conformational change from a duplex to a cruciform structure of two hairpins (McMurray et al., Proc. Natl. Acac. Sci. 88, 666 [1991]; Gacy and McMurray, Biochemistry 33, 11951 [1994]; and McMurray et al., Biochemistry 33, 11960 [1994]). Within the enkephalin enhancer, mutations, which stabilize or destabilize a cruciform structure, resulted in increased or decreased transcription, respectively, without affecting the transcription factor binding (Comb et al., EMBO J. 7, 3793 [1988]).

In the presently claimed invention, hairpin oligonucleotides, containing a duplex portion with a CRE, were introduced into cells and successfully functioned as decoys to alter gene expression.

In yet other embodiments, two hairpin forming synthetic oligonucleotides, each containing one of the sense- and antisense-cis-elements, respectively, and complementary to the other, in combination form a cruciform DNA. Such cruciform DNA can increase the potency of the transcription factor decoy to inhibit gene transcription. Similar DNA structures are known to be generated during genetic recombination (See e.g., Holliday, Genet. Res. 5, 282 [1964]; Dressler and Potter, Annu. Rev. Biochem. 51, 727 [1982]; Gellert et al., Cold Spring Harbor Symp. Quant. Biol. 43, 35 [1978]; and Panayotatos and Wells, Nature 289, 466 [1981]) and from palindromic sequences under the effect of supercoiling (See e.g., Panayotatos and Fontaine, J. Biol. Chem. 262, 11364 [1987]; and Horwitz and Loeb, Science 241, 703 [1988]), indicating a biological role for such structures.

FIG. 1 presents a model for cruciform decoys. This model is supported by work conducted on the enkephalin enhancer (Gacy and McMurray, Biochemistry 33, 11951 [1994]; and McMurray et al., Biochemistry 33, 11960 [1994]). The hairpin decoys exert strong binding affinity for the transcription factors as shown in FIG. 1(II), whereas duplex decoys are weak binding decoys (FIG. 1(B)). The linear duplex exhibits poor binding for CREB and CREB preferentially bound and stabilized the hairpin form of the enhancer (Gacy and McMurray; and McMurray et al., supra). While the present invention is not limited to any particular mechanisms, the transcription factor binding may stabilize the hairpin decoys and facilitate further binding of additional factors by inducing conformational changes as shown in FIG. 1 (III and IV). The acidic pH facilitates and stabilizes the hairpin structure, and protein binding stabilizes the hairpin state due to its negative charge and/or by phosphorylation that increases the net negative charge around the enhancer (McMurray et al., Proc. Natl. Acad. Sci. 88, 666 [1991]). The probability of duplex decoy (FIG. 1(A)) formation from the hairpin decoy (FIG. 1(I)) is small even in the absence of a stabilizing protein. It is shown that the hairpin state, once formed, shows a persistent stability even under conditions where the free energy difference between cruciform and duplex states favors the duplex (Gacy and McMurray; and McMurray et al., supra). The probability of hairpin decoy (FIG. 1(I)) formation from duplex decoy (FIG. 1(A)) is small because the activation energy for the forward reaction, the hairpin formation from a linear duplex, is higher than that for the reverse reaction at neutral pH (Gacy and McMurray; and McMurray et al., supra). The spontaneous interconversion between the protein-bound duplex state (FIG. 1(B)) and protein bound cruciform (FIG. 1(II)) is unlikely.

Because the probability of hairpin formation from a stable duplex of cellular cis-transcription element is small at neutral pH, and because the hairpin oligonucleotide may have a higher affinity for the transcription factor than the linear DNA, the exogenously supplied hairpin decoy oligonucleotide would be a more efficient competitor for the binding of cellular transcription factors than a linear duplex decoy, and thereby can interfere with transcription more efficiently in vivo.

The presently claimed invention contemplates all oligonucleotide structures that contain a CRE or similar sequence. These structures include, but are not limited to, linear duplex, hairpin, stem-loop, cruciform, bent, and any other secondary, tertiary, or quaternary structures.

In one embodiment of the presently claimed invention, a 24-mer CRE perfect palindrome oligonucleotide that is capable of forming a hairpin, 5'-TGACGTCATGACGTCATGACGTCA-3' (SEQ ID NO:2), or a non-palindromic hairpin forming oligonucleotide, 5'-GCTGACGTCGGCCTGACGTCAGC-3' (SEQ ID NO:3), penetrated into treated cells and competed with the cellular cis-element for the binding of sequence-specific CRE DNA-binding proteins, such as the 43 kDa CREB. The palindromic or hairpin-forming CRE oligonucleotide interfered with CRE-directed transcription in intact cells as determined by a transient transcription assay. The 24-mer CRE palindrome oligonucleotide produced potent growth inhibition in a variety of cancer cells including breast, prostate, lung, ovarian, colon, and epidermoid carcinomas, and multidrug-resistant (MDR) cancer cell lines of MCF7-TH (MDR-breast cancer) and HCT-15 (MDR-colon carcinoma). The growth of normal human mammary epithelial, lung epithelial, and human newborn foreskin fibroblast (i.e., HS68 cells) cell lines was not affected by the CRE oligonucleotide. Treatment of nude mice bearing HCT-15 MDR colon carcinoma with 24-mer CRE oligonucleotide resulted in a potent inhibition of tumor growth. The CRE-oligonucleotide-induced growth inhibition accompanied changes in cell morphology and the appearance of apoptotic nuclei.

In other embodiments, the hairpin-forming oligonucleotide SEQ ID NO:10 demonstrated a strong inhibition of CRE-directed transcription in intact cells and showed very strong growth inhibition (i.e., 70–80%). SEQ ID NO:11, the complement of SEQ ID NO:10, gave weaker growth inhibition (i.e., 30%). Treatment with a combination of SEQ ID NO:10 and SEQ ID NO:11 gave over 80% growth inhibition. These oligonucleotides have a CRE sequence that differs from the CRE consensus sequence (i.e., SEQ ID NO:1). These data demonstrate that hairpin forming oligonucleotides can act as strong decoys, that sequences that deviate from the CRE consensus can act as strong decoys, and that a range of decoy potencies can be achieved for tailoring the desired competitive impact.

To demonstrate that the nucleotide sequence, and not the secondary structure alone, was required for decoy function, cells were treated with a nonsense sequence palindromic oligonucleotide (i.e., an oligonucleotide comprising a perfect palindrome that forms a hairpin structure, but with no CRE sequence similarity). Such nonsense structural control oligonucleotides did not function as CRE decoys (i.e., did not compete with native CRE sequences for binding to transcription factors).

Although the present invention is not limited to any particular mechanism, other control experiments suggested that the decoys bind to the transcription factor DNA-binding domain. First, undifferentiated F9 teratocarcinoma cells, a cell line that is unresponsive to cAMP, were treated with CRE decoys and no growth inhibition was observed. These results suggest that the decoys may act as growth inhibitors, at least in part, through binding to CREB because the F9 cells are CREB deficient (Gonzalez and Montminy, Cell 59, 675 [1989]). Second, KCREB, a CREB mutant that contains a mutation of a single amino acid in the DNA-binding domain, is known not to bind to native CRE sequences (Walton et al., Mol. Endocrinol. 6, 647 [1992]). Cancer cells harboring KCREB exhibited decreased cell growth, and showed decreased CRE-protein binding upon CRE decoy treatment as compared to parental cells, indicating that the DNA binding domain was the region of interaction between the decoys and CREB-like transcription factors.

The data show that the CRE-transcription factor decoy can modulate in vivo gene transcription and restrain tumor growth in vivo. Thus, this technology offers great promise as a tool for treating diseased conditions and can also be used for defining cellular regulatory processes.

The specificity of the growth inhibitory effect of the decoy oligonucleotides against CRE-transcription factors on cancer cells is supported by several lines of evidence; (i) multiple different CRE decoy oligonucleotides produced potent growth inhibition of cancer cells but not normal cells, in vitro and in vivo, whereas, mismatched control oligonucleotides (i.e., oligonucleotides similar to the decoys but containing mismatched nucleotide pairs, such that self-hybridization does not occur—non-duplex oligonucleotides) did not inhibit growth; (ii) the administration of CRE decoy oligonucleotides, but not mismatched oligonucleotides, markedly inhibited CRE DNA-protein complex formation and CRE-directed transcription activity in both cancer cells and normal cells; (iii) cellular uptake of decoy oligonucleotides and mismatched oligonucleotides was similar for cancer cells and normal cells; and (iv) the specific growth inhibitory effect toward cancer cells correlated with induction of cell differentiation/apoptosis.

As described in the Examples provided below, a variety of methods can be used to deliver the decoys of the presently claimed invention into target cells. Methods for in vivo and/or in vitro delivery include, but are not limited to, oral intake, injection (e.g., subcutaneous, intraperitoneal, intramuscular, or other injection methods), direct exposure in aqueous or media solution, transfection (e.g., calcium phosphate, electroporation, DEAE-dextran based, and lipid mediated), transgenic expression (e.g., a decoy expression system delivered by microinjection, embryonic stem cell generation, or retroviral transfer), or any of the other commonly used nucleic acid delivery systems known in the art.

A sufficient concentration of decoys can be added to target cells to guarantee significant competition with native enhancer sequences. For example, it has been estimated that when 10 $\mu$M of phosphorothioate modified oligonucleotide are incubated with $2.5 \times 10^6$ cells/ml, there are $10^7$ to $10^8$ molecules of the oligonucleotide per cell (Bielinska el al., Science 250, 997 [1990]). If only a small fraction of these penetrated into the cell nuclei (e.g., 10%), each cell would contain over a million copies of the oligonucteotide. This is in 100 to 1000-fold excess over the likely number of transcription factors present in a given cell (Lenardo et al., Proc. Natl. Acad. Sci. 85, 8825 [1988]).

In addition to providing an effective means of controlling cancer cell proliferation, the CRE decoy oligonucleotides of the present invention will find use in many other applications. A large number of genes are transcriptionally regulated through cAMP response elements. Many of these gene encode for regulatory molecules that control the expression of other genes. For example, CREB interacts with CBP which is involved in the transcriptional activation of p53 (Gu el al., Nature 387, 819 [1997]). In addition, CREB is known to associate with (e.g., heterodimerize) a variety of other transcription factors (e.g., members of the Jun/Fos family, Nilsson et al., Cell Growth and Differentiation 8, 913 [1997]; and CBP, which can be competitively bound away from other transcription factors that it co-activates such as AP-1 and PARs, Agadir et al., Cancer Research 57, 3444 [1997]).

One of many possible examples for further use of CRE decoys is in the regulation of hepatitis B virus metabolism. The X gene product (i.e., pX) of the hepatitis B virus is an important transactivator of a variety of viral and cellular genes (Williams and Andrisani, Proc. Natl. Acad. Sci. 92, 3819 [1995]). pX has been shown to interact with transcription factors that bind to CREs such as CREB and ATF. The use of CRE decoys may help prevent pX action and thus interfere with the virus life cycle. CRE-like sequences have also been identified in the promoters of other viruses (e.g., HTLV-1).

Surprisingly, the decoys of the present invention were also found to inhibit protein kinase A (PKA) activity in decoy-treated cancer cells but not normal cells. Cultured ovarian cancer cells were treated with and without CRE decoy oligonucleotide using the methods of Example 1 below. Extracts were analyzed by column chromatography for PKA activity. Untreated cancer cells demonstrated two peaks corresponding to Type-1 and Type-2 PKA, while CRE decoy-treated cells exhibited no peaks (i.e., PKA activity was wiped out). HS68 cells (i.e., non-cancerous cells) did not show any differences in PKA activity between treated and untreated samples. These data demonstrate that CRE-decoy oligonucleotides inhibit PKA activity in cancer cells but not in normal cells.

Thus, by targeting the desired cells with appropriate exposure (i.e., time, concentration, and affinity) of decoy, the present invention provides a means of regulating many physiological and cellular processes that are mediated by cAMP.

Experimental

The following examples are provided in order to demonstrate and further illustrate certain preferred embodiments and aspects of the present invention and are not to be read as limiting the scope thereof.

In the experimental disclosure which follows, the following abbreviations apply: ° C. (degrees Centigrade); rpm (revolutions per minute); IM (intramuscular); IP (intraperitoneal); IV (intravenous or intravascular); SC (subcutaneous); H$_2$O (water); aa (amino acid); bp (base pair); kb (kilobase pair); kD (kilodaltons); gm (grams); µg (micrograms); mg (milligrams); ng (nanograms); µl (microliters); ml (milliliters); mm (millimeters); nm (nanometers); µm (micrometer); M (molar); mM (millimolar); µM (micromolar); nM (nanomolar); U (units); V (volts); MW (molecular weight); µCi (microcurrie); sec (seconds); min(s) (minute/minutes); hr(s) (hour/hours); ab (antibody); IC$_{50}$ (50% inhibitory concentration); CRE (cAMP response element); CREB (cAMP response element-binding protein); DOTAP (N-[1-(2,3-Dioleoyloxy)propyl]-N,N,N-trimethylammonium methysulfate); DTT (dithiothreitol); HCl (hydrochloric acid); MgCl$_2$ (magnesium chloride); KCl (potassium chloride); NaCl (sodium chloride); OD$_{280}$ (optical density at 280 nm); OD$_{600}$ (optical density at 600 nm); PAGE (polyacrylamide gel electrophoresis); PBS (phosphate buffered saline [150 mM NaCl, 10 mM sodium phosphate buffer, pH 7.2]); PCR (polymerase chain reaction); PEG (polyethylene glycol); PMSF (phenylmethylsulfonyl fluoride); RT-PCR (reverse transcription PCR); SDS (sodium dodecyl sulfate); Tris (tris(hydroxymethyl)aminomethane); EDTA (Ethylenediaminetetraacetic Acid); w/v (weight to volume); v/v (volume to volume); MDR (multidrug-resistant); MCF7 (human breast adenocarcinoma cells); MCF10A (human mammary gland cells); LNCaP (human metastatic prostate adenocarcinoma); A549 (human lung carcinoma cells); OVCAR 8 (human ovarian carcinoma cells); LS 174T (human colon adenocarcinoma cells); KB (human epidermoid carcinoma cells); HCT-15 (MDR human colon adenocarcinoma cells); MCF7-TH (MDR-breast cancer cells); L-132 (human embryonic lung cells); Bio-Rad (BioRad, Richmond, Calif.); and Sigma (Sigma Chemical Co., St. Louis, Mo.).

Oligonucleotides comprising the following sequences were used in the Examples below.

24-mer CRE-palindrome (SEQ ID NO:2):
  5'-TGACGTCA TGACGTCA TGACGTCA-3'

24-mer CRE-palindrome control (SEQ ID NO:8):
  5'-TGTGGTCA TGTACGTCA TGTGGTCA-3'

23-mer CRE-hairpin (SEQ ID NO:3):
  5'-GCTGACGTCGGCCTGACGTCAGC-3'

23-mer CRE-hairpin (SEQ ID NO:9):
  5'-GCTGACCACGCCGTGTGGTCAGC-3'

24-mer CRE-hairpin (SEQ ID NO:10):
  5'-TGCCGTCATGCCGTCATGCCGTCA-3'

24-mer CRE-hairpin (SEQ ID NO:11):
  5'-TGACGGCATGACGGCATGACGGCA-3'

EXAMPLE 1

CRE-decoy Oligonucleotide Inhibited CRE DNA-protein Complex Formation

A 24-mer single strand oligonucleotides comprising a CRE palindrome (i.e., multiple copies of a CRE consensus sequence) were introduced into a variety of culture cells. The oligonucleotide, 5'-TGACGTCATGACGTCATGACGTCA-3' (SEQ ID NO: 2), can contain unmodified phosphodiester bonds, or can contain phosphorothioate, phosphoramidite, methyl phosphonate derivatives, or other modifications to help provide stability and facilitate entry into the cells. Because the CRE oligonucleotide is palindromic, it can self-hybridize to form a duplex and provide a binding site for transcription factors that interact with CREs, including, but not limited to, the 43 kDa CREB (CRE binding protein) (Montminy and Bilezikjian, Nature 328, 175 [1987]).

Cells were treated with saline (i.e., control cells), the CRE 24-mer (150 nM for 2 days), or a control oligonucleotide and nuclear extracts were prepared using the method of Dignam (Dignam et al., Nucleic Acid Res. 11, 1475 [1983]). The control oligonucleotide was 5'-TGTGGTCATGTGGTCATGTGGTCA-3' (SEQ ID NO: 8), which is a copy of the CRE 24-mer with two mismatched bases included in each consensus sequence motif (i.e., it will not bind as well to transcription factors as will the consensus sequence oligonucleotide). Nuclear extracts were obtained from the cells and were analyzed by a mobility shift assay to compare the amount of CRE-protein bound complex between treated, untreated, and control samples. The DNA binding assay was performed by a method modified from that of Fried and Crothers (Fried and Crothers, Nucleic Acid Res. 9, 6506 [1981]). Briefly, nuclear extracts (10 µg protein) were pre-incubated with poly(dI-dC)• poly (dI-dC) (1 µg), DTT (0.3 mM), and binding buffer (12 mM Tris pH 7.9, 2 mM $MgCl_2$, 60 mM KCl, 0.12 mM EDTA, and 12% glycerol) with or without antiserum (2–4 µl) for 30 min at 4° C. $^{32}$P-labeled oligonucleotide (double-stranded CRE triplet, 5'-CCTGACGTCATGACGTCATGACGTCA-3'; SEQ ID NO:12) was then added and the reaction mixtures were incubated for 10 min at 37° C. The reaction mixtures were then separated on a 4% polyacrylamide gel at 200 V for 1.5 hours. The gel was dried and autoradiographed. AbCREB, a CREB antibody, was added to determine the presence of CREB protein within the labeled protein-DNA complexes.

Figure 2:
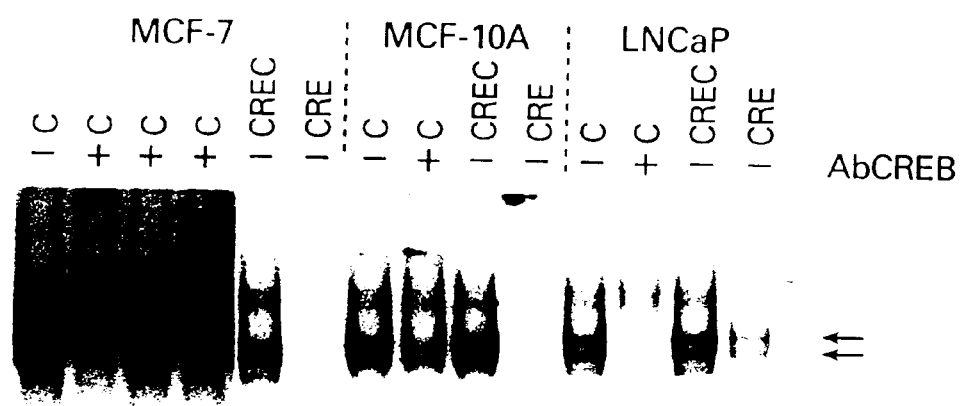
FIG. 2 shows a photograph of CRE-oligonucleotide decoy inhibition of CRE(DNA)-protein complex formation.

As shown in FIG. 2, the nuclear extracts from cells treated with the 24-mer CRE oligonucleotide demonstrated a marked decrease in formation of the CRE-protein complex in the mobility shift assay compared to untreated cells. In this figure, saline treated cells are represented by "C," CRE 24-mer treated cells by "CRE," and control 24-mer treated cells by "CREC." Samples that were treated with AbCREB antibody are designated with a "+." The two arrows designate the locations of the CRE-protein complex on the gel. As is clear from the FIG. 2, the nuclear extracts from cells treated with the two-base mismatched control oligonucleotide showed the same or similar intensity band of CRE-protein complex as that demonstrated by the nuclear extracts of saline treated cells. These results were demonstrated in MCF7 (breast cancer), MCF10A (normal human mammary epithelial cell), and LNCaP (prostate cancer) cell lines.

This Example provides a screening method to assay oligonucleotide candidates for their decoy capabilities and efficiencies. A candidate can be tested in place of the 24-mer (SEQ ID NO: 2) as described above. The percentage inhibition of transcription factor binding to the $^{32}$P-labeled CRE oligonucleotide (double-stranded CRE triplet, 5'-CCTGACGTCATGACGTCATGACGTCA-3'; SEQ ID NO:12) can be calculated and decoy efficiency thus determined. For determination of binding competition to transcription factors other than CREB, other antibodies can be used (e.g., antibodies raised against cyclic AMP-responsive element modulators (CREMs), ATF-1, Tax, pX, C/EBPs, Jun, Fos, CBP, or other desired transcription factors or proteins).

EXAMPLE 2

CRE-decoy Oligonucleotide Interfered with CRE-directed Transcription

The CRE oligonucleotide successfully interfered with the CRE-directed transcription in intact cells. To analyze the effect of CRE oligonucleotide in CRE-directed transcription, a transient transcription assay was performed using a reporter plasmid, somatostatin Δ-71 (CPE-containing promoter)-CAT (chloramphenicol acetyltransferase) fusion gene (Montminy et al., Proc. Natl. Acad. Sci. 83, 6682 [1986]). MCF7 cells were transfected with 5 µg of somatostatin-chloramphenicol acetyltransferase fusion gene (Δ-71 SS-CAT plasmid) and 4 µg of CRE (i.e., the 24-mer described in Example 1) or control oligonucleotide by the use of transfection reagent N-[1-(2,3-Dioleoyloxy)propyl]-N,N,N-trimethylammonium methysulfate (DOTAP). After 5 hours, fresh medium was added, and the cells were harvested at 48 to 72 hours, then assayed for CAT activity. Some samples were also treated with forskolin (10 µM), an compound with adenyl cyclase activating properties (i.e., a compound that increases intracellular cAMP concentrations), for the final 24 hours. Cell lysates were prepared as described by Gorman (Gorman, High efficiency gene transfer into mammalian cells, DNA Cloning, Vol II, pp 143–165, IRL press, Oxford, England [1985]). Lysates (75 µg of protein) were incubated with 0.4 µCi of [$^{14}$C] chloramphenicol, 0.53 mM acetyl-CoA, and 250 mM Tris-HCl, pH 7.8 for 90 minutes at 37° C. Under these conditions, CAT activity was linear with time. Reaction products were analyzed by thin-layer chromatography (Gorman, supra).

Figure 3:
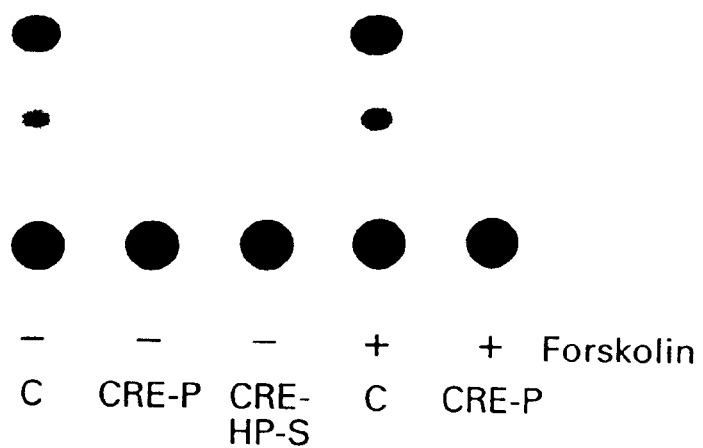
FIG. 3 shows data obtained from thin-layer chromatography of CRE-oligonucleotide decoy inhibition of CRE-directed transcription.

As shown in FIG. 3, transfection of cells with Δ-71 CAT plus the single stranded CRE palindrome oligonucleotide resulted in a greater than 90% inhibition of the CRE-directed transcription compared to cells transfected with Δ-71 CAT alone. In this Figure, C represents control cells treated with saline and the Δ-71 CAT alone and CRE-P represents cells treated with the CRE palindrome oligonucleotide and Δ-71 CAT. The lane labeled CRE-HP-S represents cells treated with Δ-71 CAT and single stranded oligonucleotide that forms a hairpin loop, 5'-TGCCGTCATGCCGTCATGCCGTCA-3' (SEQ ID NO:10), where the double-stranded stem forms a CRE binding site (i.e., CRE transcription factors should bind to it). Lanes labeled with a "+" had forskolin added to them for the final 24 hours. Addition of the two-base mismatched control oligonucleotide (i.e., the control oligonucleotide described in Example 1), which does not self-hybridize to form a duplex, had no inhibitory effect on the CAT activity. However, the 24-mer CRE-hairpin sense oligonucleotide strongly inhibited CAT activity. These results were also demonstrated in MCF10A and LNCaP cells.

EXAMPLE 3

Cellular Uptake of CRE-decoy Oligonucleotide

To examine the efficacy of cellular incorporation of the CRE oligonucleotides, we incubated $^{32}$P-labeled samples of CRE-palindrome oligonucleotide and control oligonucleotide with MCF7 and MCF10A cells. Cell-associated radio-activity was quantified. Within 5 hrs, about 10% of the total input oligonucleotide accumulated in the cell and the incorporation continued to rise thereafter reaching 20–25% maximum levels at 24 hr of oligonucleotide incubation. The amounts and the rates of the incorporation of oligonucleotide were similar between MCF7 and MCF10A cells and between the CRE-decoy oligonucleotide and control oligonucleotide.

EXAMPLE 4

CRE-decoy Oligonucleotide Inhibited Cancer Cell Growth In Vitro

The 24-mer CRE palindrome oligonucleotide produced potent growth inhibition in a variety of cancer cells including MCF7 (breast cancer), LNCaP (prostate cancer), A549 (lung carcinoma), OVCAR 8 (ovarian carcinoma), LS174T (colon carcinoma), KB (epidermoid carcinoma), and multidrug-resistant (MDR) cancer cell lines of MCF7-TH (MDR-breast cancer) and HCT-15 (MDR-colon carcinoma). Importantly, the growth of normal cells, MCF10A (human mammary epithelial cell) and L-132 (human lung epithelial cell) was not affected by the CRE oligonucleotide.

Cells (0.25–1×10$^5$/well) were plated in a 6-well plate containing the growth medium at 37° C. The 24-mer-CRE palindrome oligonucleotide (i.e., as described in Example 1) or two-base mismatched control oligonucleotide (i.e., as described in Example 1) was added, one day after seeding, to duplicate wells at varying concentrations. To increase the delivery of oligonucleotides into the cell, transfection reagent DOTAP was added along with the oligonucleotides. Saline treated (untreated), DOTAP treated (0 concentration), CRE, or CRE control oligonucleotide treated cells were harvested after 4 days of treatment, and cell numbers were counted in duplicate by a Coulter Counter. Data, as shown in FIG. 3, represent mean ±S.D. obtained from 3 separate experiments. In this figure, lines with closed circles represent cells treated with the 24-mer-CRE palindrome oligonucleotide, while lines with open boxes represent cells treated with the control, mismatch oligonucleotide.

Figure 4:
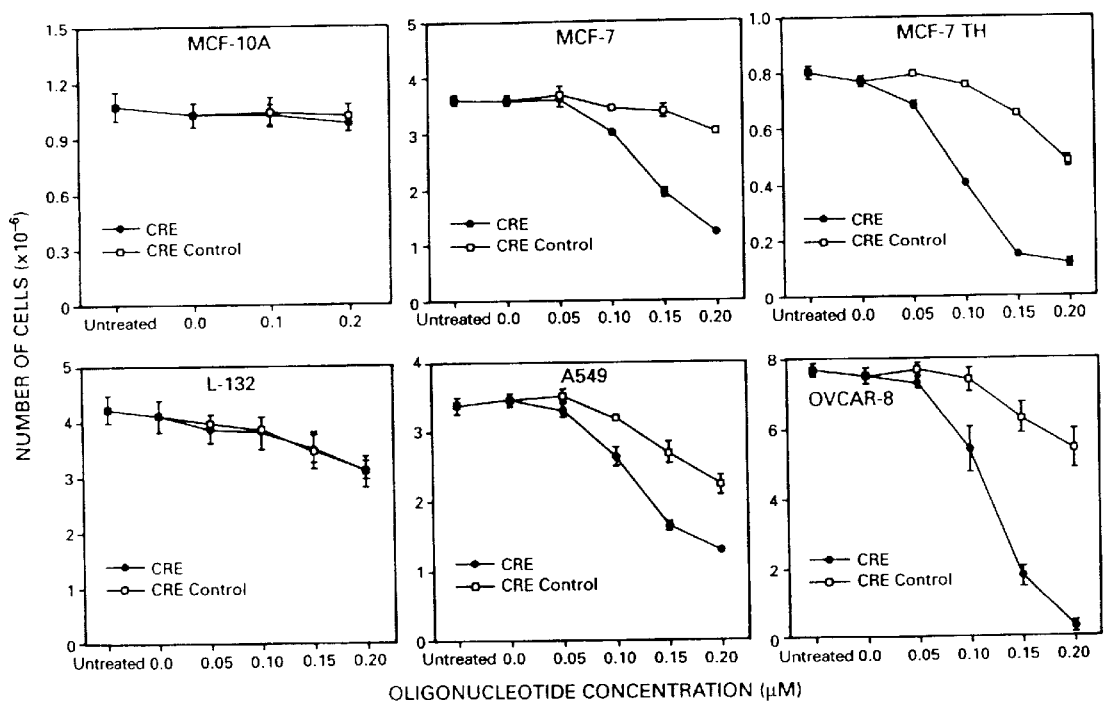
FIG. 4 shows CRE-oligonucleotide decoy inhibition of cancer cell growth in vitro in several different cell lines.

As shown in FIG. 4, the growth inhibition of cancer cells was achieved at nanomolar concentrations of CRE oligonucleotide ($IC_{50}$, 100–150 nM). As shown, growth was inhibited in each of the cancer cell lines, but was unaffected in the normal cells (i.e., MCF-10A and L-132 cells). The growth inhibition was CRE-sequence specific as the two-base mismatched control oligonucleotide had no growth inhibitory effect. In separate experiments, the 24-mer CRE-hairpin sense and antisense oligonucleotides at 150 nM concentration demonstrated 70% and 30% growth inhibition, respectively, and in combination produced over 80% growth inhibition.

EXAMPLE 5

CRE-decoy Oligonucleotide Inhibited Tumor Growth In Vivo

HCT-15 human MDR colon carcinoma tumor cells ($2 \times 10^6$ cells) were inoculated subcutaneously into the left flank of athymic mice. The CRE or control oligonucleotide was injected intraperitoneally into mice at 0.01–0.1 mg/0.1 ml saline/mouse, daily, 5×/week for 4 weeks, when tumor size reached 30–50 mg ~10 days after cell inoculation. Tumor volumes were obtained from daily measurements of the longest and shortest diameters and calculated by the formula, $4/3\pi r^3$ where r=(length+width)/4.

Figure 5:
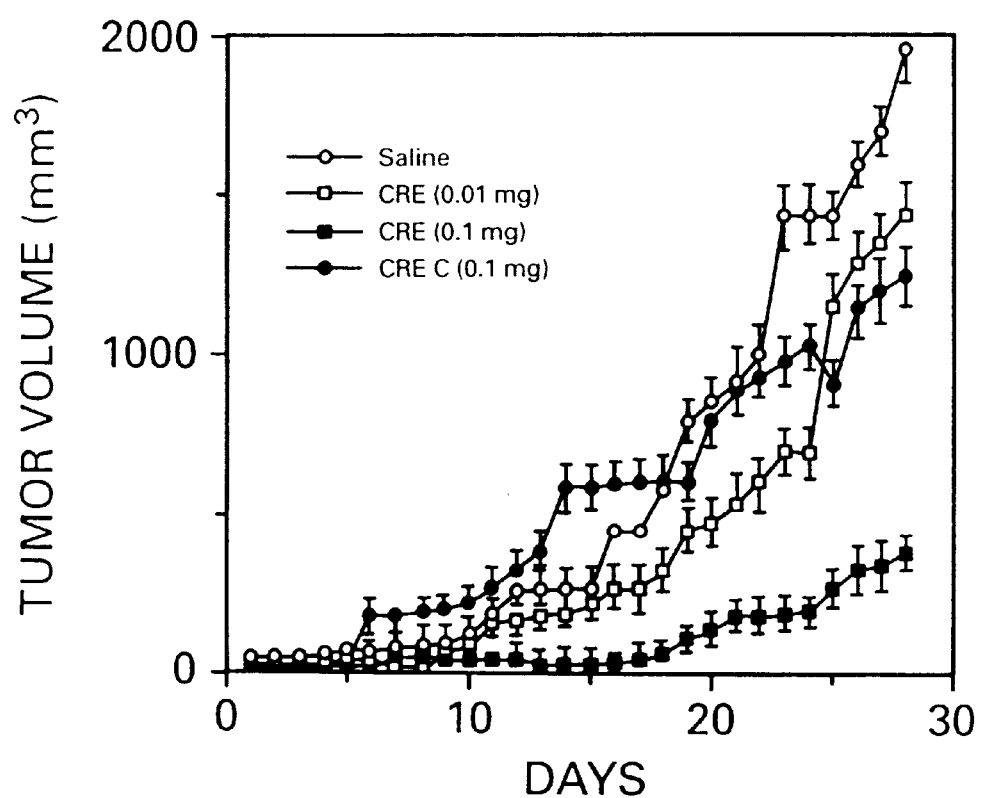
FIG. 5 shows CRE-oligonucleotide decoy inhibition of tumor growth in vivo by measuring tumor volume.

As shown in FIG. 5, treatment of nude mice bearing HCT-15 human MDR colon carcinoma with 24-mer CRE oligonucleotide (open boxes=0.01 mg; closed boxes=0.1 mg) resulted in greater than 85% inhibition of tumor growth as compared to the saline treated control tumors (open circles), without causing toxicity. Two-base mismatched control oligonucleotide (closed circles) had no growth inhibitory effect. Data represent means ±S.D. of 5–7 tumors in each group.

EXAMPLE 6

CRE-oligonucleotide Treatment Induced Differentiation/apoptosis

Figure 6:
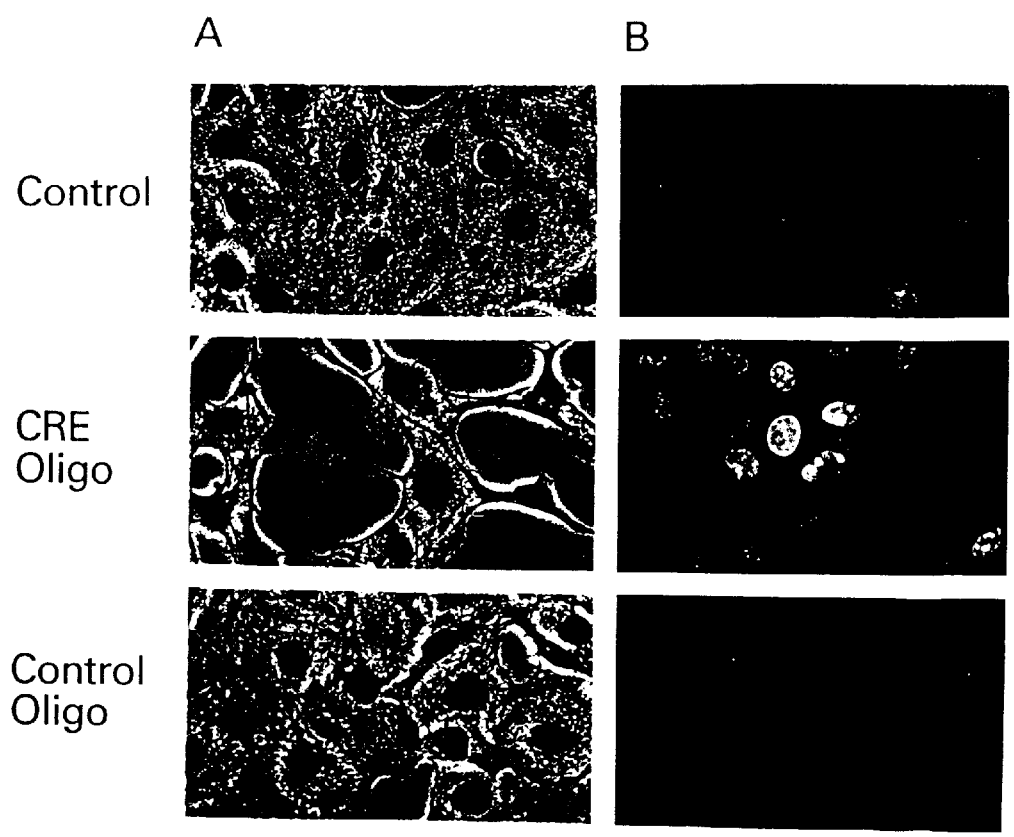
FIG. 6 shows CRE-oligonucleotide decoy induction of apoptosis as demonstrated by: A) whole cell morphology; and B) nuclear morphology.

CRE-oligonucleotide treatment resulted in changes in cell morphology and appearance of apoptotic nuclei (OVCAR 8), as shown in FIG. 6. The changes in cell morphology and apoptotic nuclei were not observed in the saline or control oligonucleotide treated cells. To examine whole cell morphology, OVCAR8 cells, untreated (Control) or treated with CRE-palindrome oligonucleotide (CRE Oligo; as described in Example 1) or control oligonucleotide (Control Oligo; as described in Example 1), were washed with PBS, fixed with 70% methanol for 5 min, and stained with Giemsa (Bio-Rad) for 15 min. FIG. 6, section A, shows whole cell morphology. After staining, the whole cells were visualized under an inverted microscope at ×240. As shown, cells treated with the CRE decoy oligonucleotides exhibited the characteristics of apoptotic cells (e.g., loss of cell junctions, loss of micovilli, condensed cytoplasm, margination of nuclear chromatin into discrete masses, compacting of mitochondria and ribosomes, dilation of the endoplasmic reticulum, and break-up of cells into several membrane bound bodies), while cells treated with the mismatch oligonucleotides appeared similar to the untreated cells. FIG. 6, section B shows nuclear morphology. To assay nuclear morphology (i.e., apoptotic nuclei), cells were washed with PBS, fixed with 70% ethanol for 1 hr, and stained with 1 mM Hoechst 33258 (Sigma) for 30 min (Oberhammer el al., Proc. Natl. Acad. Sci. 89, 5408 [1992]). The nuclear morphology of cells was visualized by a fluorescence microscope (Olympus BH2) at ×2600. As shown, nuclei from cells treated with the CRE decoy oligonucleotides exhibited the characteristics of apoptotic nuclei, while nuclei from cells treated with the mismatch oligonucleotides appeared similar to the untreated nuclei.

The bcl-2 protein promotes cell survival (Vaux et al., Nature 335, 440 [1988]) by inhibiting the process of apoptosis (Haldar et al., Arch. Biochem. Biophys. 315, 483 [1994]; and Miyashita and Reed, Blood 11, 151 [1993]). MCF7 cells have been shown to express an increased level of bcl-2 protein (Haldar et al., Cancer Res. 54, 2095 [1994]), consistent with their cancerous phenotype.

Figure 7:
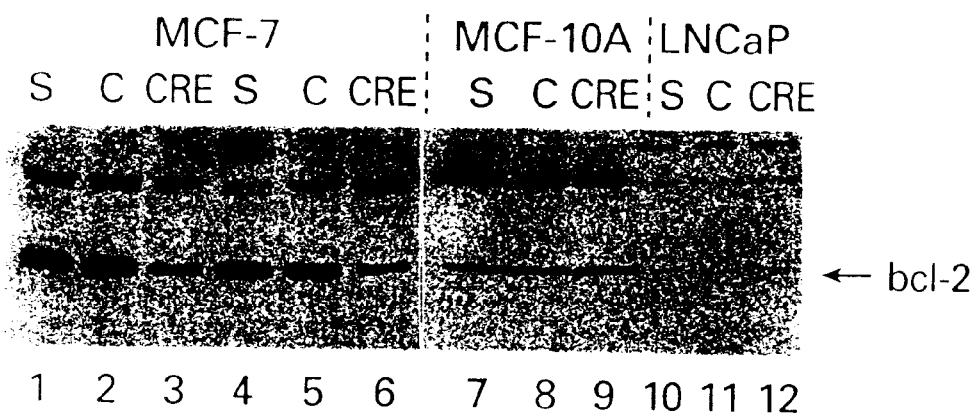
FIG. 7 shows Bcl-2 protein levels in CRE-oligonucleotide treated cells and control cells as measured by Western blot analysis.

Bcl-2 protein levels were measured by standard western blotting techniques known in the art using Anti-bcl-2 antibody. As shown in FIG. 7, CRE-decoy oligonucleotide treatment markedly reduced bcl-2 level in MCF7 cells. Lanes marked "S" were from saline treated cells, "CRE" from CRE-palindrome oligonucleotide (150 nM, 4 days) treated cells, and "C" from CRE-control oligonucleotide treated cells. The normal mammary epithelial cell line, MCF-10A, contained a low level of bcl-2, and the CRE oligonucleotide treatment did not alter the bcl-2 level in these normal cells. The control oligonucleotide had no effect on bcl-2 protein level in any of the cell types.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A method for regulating gene transcription in target cells comprising:
   a) providing:
      i) one or more cAMP response element decoys comprising nucleic acid molecules, wherein said nucleic acid molecules are selected from the group consisting of SEQ ID NO: 3 and two hairpin-forming oligonucleotides complementary to one another in a manner wherein combining said hairpin-forming oligonucleotides produces a cruciform structure; and
      ii) one or more target cells, wherein said target cells contain cAMP response element enhancer DNA and one or more transcription factors that associate with said cAMP response element enhancer DNA; and
   b) exposing said target cells to said cAMP response element decoys under conditions such that said cAMP response element decoys compete with said cAMP response element enhancer DNA for binding to said one or more transcription factors.

2. The method of claim 1, wherein said two hairpin-forming oligonucleotides comprise SEQ ID NO:10 and SEQ ID NO:11.

3. The method of claim 1, wherein said cAMP response element decoys contain modified phosphodiester bonds.

4. The method of claim 3, wherein said modified phosphodiester bonds are selected from the group consisting of phosphorothioate, phosphoramidite, and methyl phosphate derivatives.

5. The method of claim 1, wherein said target cells comprise cancer cells.

6. The method of claim 1, wherein said exposing is selected from the group consisting of injection, direct exposure, oral intake, transfection, and transgenic expression.

7. A composition comprising one or more purified nucleic acid molecules that compete with cAMP response element enhancer DNA for binding to one or more transcription factors, wherein said nucleic acid molecules are selected from the group consisting of SEQ ID NO:3 and cruciform structures comprising first and second hairpin-forming oligonucleotides.

8. The composition of claim 7, wherein said first and second hairpin-forming oligonucleotides comprise SEQ ID NO:10 and SEQ ID NO:11.

9. The composition of claim 7, wherein said nucleic acid molecules contain modified phosphodiester bonds.

10. The composition of claim 9, wherein said modified phosphodiester bonds are selected from phosphorothioate, phosphoramidite, and methyl phosphate derivatives.

11. A method for regulating cancer cell proliferation comprising:
  a) providing:
    i) one or more cAMP response element decoys comprising nucleic acid; and
    ii) one or more cancer cells, wherein said cancer cells contain cAMP response element enhancer DNA and one or more transcription factors that associate with said cAMP response element enhancer DNA; and
  b) exposing said cancer cells to said cAMP response element decoys under conditions such that said cAMP response element decoys compete with said cAMP response element enhancer DNA for binding to said one or more transcription factors causing inhibition of cancer cell proliferation.

12. The method of claim 11, wherein said cAMP response element decoys comprise DNA.

13. The method of claim 11, wherein said cAMP response element decoys comprise at least one single-stranded oligonucleotide that hybridizes to form a duplex.

14. The method of claim 13, wherein said single-stranded oligonucleotide comprises at least one palindromic sequence.

15. The method of claim 14, wherein said single-stranded oligonucleotide comprises SEQ ID NO:2.

16. The method of claim 11, wherein said cAMP response element decoys comprise at least one hairpin-forming single-stranded oligonucleotide.

17. The method of claim 16, wherein said cAMP response element decoys comprise cruciform structures comprising first and second hairpin-forming oligonucleotides.

18. The method of claim 11, wherein said cAMP response element decoys contain modified phosphodiester bonds.

19. The method of claim 18, wherein said modified phosphodiester bonds are selected from the group consisting of phosphorothioate, phosphoramidite, and methyl phosphate derivatives.

20. The method of claim 11, wherein said exposing is selected from the group consisting of injection, direct exposure, oral intake, transfection, and transgenic expression.

21. The method of claim 11, wherein said cancer cells are selected from breast, prostate, lung, ovarian, colon, and epidermoid cells.

22. A method for regulating cancer cell proliferation comprising:
  a) providing:
    i) one or more cAMP response element decoys comprising nucleic acid, wherein said nucleic acid molecules comprises at least one hairpin-forming single-stranded oligonucleotide, wherein said hairpin-forming single-stranded oligonucleotide comprises SEQ ID NO:3; and
    ii) one or more target cells, wherein said target cells contain cAMP response element enhancer DNA and one or more transcription factors that associate with said cAMP response element enhancer DNA; and
  b) exposing said target cells to said cAMP response element decoys under conditions such that said cAMP response element decoys compete with said cAMP response element enhancer DNA for binding to said one or more transcription factors causing inhibition of cancer cell proliferation.

23. A method for regulating cancer cell proliferation comprising:
  a) providing:
    i) one or more cAMP response element decoys comprising nucleic acid, wherein said nucleic acid molecules comprises at least one hairpin-forming single-stranded oligonucleotide, wherein said oligonucleotide comprise cruciform structures comprising first and second hairpin-forming oligonucleotides, wherein said first hairpin-forming oligonucleotide comprises SEQ ID NO:10 and said second hairpin-forming oligonucleotide comprises SEQ ID NO:11; and
    ii) one or more target cells, wherein said target cells contain cAMP response element enhancer DNA and one or more transcription factors that associate with said cAMP response element enhancer DNA; and
  b) exposing said target cells to said cAMP response element decoys under conditions such that said cAMP response element decoys compete with said cAMP response element enhancer DNA for binding to said one or more transcription factors causing inhibition of cancer cell proliferation.

* * * * *